US010815653B2

(12) United States Patent
Hird

(10) Patent No.: US 10,815,653 B2
(45) Date of Patent: *Oct. 27, 2020

(54) ABSORBENT ARTICLE COMPRISING A SYNTHETIC POLYMER DERIVED FROM A RENEWABLE RESOURCE AND METHODS OF PRODUCING SAID ARTICLE

(71) Applicant: The Procter & Gamble Company, Cincinnati, OH (US)

(72) Inventor: Bryn Hird, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/667,960

(22) Filed: Oct. 30, 2019

(65) Prior Publication Data

US 2020/0063416 A1 Feb. 27, 2020

Related U.S. Application Data

(63) Continuation of application No. 16/194,670, filed on Nov. 19, 2018, now Pat. No. 10,501,920, which is a
(Continued)

(51) Int. Cl.
*E03D 1/35* (2006.01)
*A61F 13/84* (2006.01)
(Continued)

(52) U.S. Cl.
CPC .......... *E03D 1/35* (2013.01); *A61F 13/15203* (2013.01); *A61F 13/15617* (2013.01);
(Continued)

(58) Field of Classification Search
CPC ................. E03D 1/35; A61F 13/15203; A61F 13/15617; A61F 13/551; A61F 13/84;
(Continued)

(56) References Cited

U.S. PATENT DOCUMENTS 2,042,224 A 5/1936 Groll Herbert et al.
3,661,875 A 5/1972 Sieja
(Continued)

FOREIGN PATENT DOCUMENTS

EP 509 708 A1 10/1992
EP 640 330 A1 3/1995
(Continued)

OTHER PUBLICATIONS

PCT International Search Report and Opinion dated Oct. 4, 2007, 11 pages.

*Primary Examiner* — William K Cheung
(74) *Attorney, Agent, or Firm* — Christian M. Best; Andrew J. Hagerty

(57) ABSTRACT

An absorbent article is disclosed having a topsheet, a backsheet joined with the topsheet, an absorbent core disposed between the topsheet and the backsheet, and a synthetic superabsorbent polymer derived from a first renewable resource via at least one intermediate compound, wherein said superabsorbent polymer exhibits a defined Saline Flow Conductivity value and Absorption Against Pressure value. Alternately, an absorbent article is disclosed having a synthetic polyolefin derived from a first renewable resource via at least one intermediate compound. The synthetic polyolefin exhibits defined performance characteristics making the polyolefin particularly useful in certain components of the absorbent article. Methods for making the aforementioned absorbent articles are also disclosed.

20 Claims, 7 Drawing Sheets

Related U.S. Application Data continuation of application No. 15/011,930, filed on Feb. 1, 2016, now Pat. No. 10,166,312, which is a continuation of application No. 12/975,914, filed on Dec. 22, 2010, now abandoned, which is a continuation of application No. 11/724,341, filed on Mar. 15, 2007, now abandoned.

(60) Provisional application No. 60/783,274, filed on Mar. 17, 2006.

(51) Int. Cl.

| | | |
|---|---|---|
| *A61L 15/28* | (2006.01) | |
| *A61L 15/40* | (2006.01) | |
| *A61L 15/24* | (2006.01) | |
| *A61L 15/60* | (2006.01) | |
| *C12P 7/42* | (2006.01) | |
| *A61F 13/15* | (2006.01) | |
| *A61F 13/551* | (2006.01) | |

(52) U.S. Cl.
CPC ............ *A61F 13/551* (2013.01); *A61F 13/84* (2013.01); *A61L 15/24* (2013.01); *A61L 15/28* (2013.01); *A61L 15/40* (2013.01); *A61L 15/60* (2013.01); *C12P 7/42* (2013.01); *C12P 2203/00* (2013.01)

(58) Field of Classification Search
CPC .......... A61F 15/24; A61F 15/28; A61F 15/40; A61F 15/60; C12P 7/42; C12P 2203/00
USPC ....................................................... 137/409
See application file for complete search history.

(56) References Cited

U.S. PATENT DOCUMENTS

| | | |
|---|---|---|
| 3,860,003 A | 1/1975 | Buell |
| 3,885,155 A | 5/1975 | Anbar |
| 4,020,780 A | 5/1977 | Shumaker et al. |
| 4,076,663 A | 2/1978 | Masuda et al. |
| 4,083,889 A | 4/1978 | Caesar et al. |
| 4,092,354 A | 5/1978 | Shiraishi et al. |
| 4,093,776 A | 6/1978 | Aoki et al. |
| 4,296,266 A | 10/1981 | Wunder et al. |
| 4,340,563 A | 7/1982 | Appel et al. |
| 4,405,297 A | 9/1983 | Appel et al. |
| 4,407,955 A | 10/1983 | Muller et al. |
| 4,423,270 A | 12/1983 | Pearson |
| 4,425,130 A | 1/1984 | Desmarais |
| 4,427,884 A | 1/1984 | Anbar et al. |
| 4,469,710 A | 9/1984 | Rielley et al. |
| 4,541,871 A | 9/1985 | Obayashi et al. |
| 4,587,308 A | 5/1986 | Makita et al. |
| 4,610,678 A | 9/1986 | Weisman et al. |
| 4,625,001 A | 11/1986 | Tsubakimoto et al. |
| 4,666,983 A | 5/1987 | Tsubakimoto et al. |
| 4,673,402 A | 6/1987 | Weisman et al. |
| 4,687,478 A | 8/1987 | Van Tillburg |
| 4,695,278 A | 9/1987 | Lawson |
| 4,729,978 A | 3/1988 | Sawicki |
| 4,734,478 A | 3/1988 | Tsubakimoto et al. |
| RE32,649 E | 4/1988 | Brandt et al. |
| 4,753,834 A | 6/1988 | Braun et al. |
| 4,786,756 A | 11/1988 | Paparizos et al. |
| 4,789,861 A | 12/1988 | Baggett et al. |
| 4,795,454 A | 1/1989 | Dragoo |
| 4,808,178 A | 2/1989 | Aziz et al. |
| 4,824,901 A | 4/1989 | Alexander et al. |
| 4,834,735 A | 5/1989 | Alemany et al. |
| 4,846,587 A | 7/1989 | Hull |
| 4,888,231 A | 12/1989 | Angstadt |
| 4,892,536 A | 1/1990 | Desmarais et al. |
| 4,909,803 A | 3/1990 | Aziz et al. |
| 4,934,535 A | 6/1990 | Muckenfuhs et al. |
| 4,940,464 A | 7/1990 | Van Gompel et al. |
| 4,966,286 A | 10/1990 | Muckenfuhs |
| 4,973,841 A | 11/1990 | Purser |
| 4,990,147 A | 2/1991 | Freeland |
| 5,036,978 A | 8/1991 | Frank et al. |
| 5,037,416 A | 8/1991 | Allen et al. |
| 5,050,742 A | 9/1991 | Muckenfuhs |
| 5,054,619 A | 10/1991 | Muckenfuhs |
| 5,092,861 A | 3/1992 | Nomura et al. |
| 5,137,537 A | 8/1992 | Herron et al. |
| 5,147,345 A | 9/1992 | Young et al. |
| 5,151,092 A | 9/1992 | Buell et al. |
| 5,164,459 A | 11/1992 | Kimura et al. |
| 5,221,274 A | 6/1993 | Buell et al. |
| 5,246,433 A | 9/1993 | Hasse et al. |
| 5,252,473 A | 10/1993 | Walkup et al. |
| 5,260,345 A | 11/1993 | Desmarais et al. |
| 5,267,992 A | 12/1993 | Van Tilburg |
| 5,269,775 A | 12/1993 | Freeland et al. |
| 5,342,338 A | 8/1994 | Roe |
| 5,387,207 A | 2/1995 | Dyer et al. |
| 5,387,720 A | 2/1995 | Neher et al. |
| 5,397,316 A | 3/1995 | Lavon et al. |
| 5,408,019 A | 4/1995 | Mertens et al. |
| 5,409,771 A | 4/1995 | Dahmen et al. |
| 5,438,194 A | 8/1995 | Koudijs et al. |
| 5,464,760 A | 11/1995 | Tsai et al. |
| 5,475,183 A | 12/1995 | Araki et al. |
| 5,554,145 A | 9/1996 | Roe et al. |
| 5,562,646 A | 10/1996 | Goldman et al. |
| 5,569,234 A | 10/1996 | Buell et al. |
| 5,571,096 A | 11/1996 | Dobrin et al. |
| 5,580,411 A | 12/1996 | Nease et al. |
| 5,607,760 A | 3/1997 | Roe |
| 5,609,587 A | 3/1997 | Roe |
| 5,625,222 A | 4/1997 | Yoneda et al. |
| 5,635,191 A | 6/1997 | Roe et al. |
| H1670 H | 7/1997 | Aziz et al. |
| 5,643,588 A | 7/1997 | Roe et al. |
| 5,661,299 A | 8/1997 | Purser |
| 5,714,156 A | 2/1998 | Schmidt et al. |
| 5,733,274 A | 3/1998 | Osborn, III |
| 5,783,504 A | 7/1998 | Ehret et al. |
| 5,836,929 A | 11/1998 | Bewick-Sonntag et al. |
| 5,865,823 A | 2/1999 | Curro |
| 5,889,072 A | 3/1999 | Chou |
| 5,897,545 A | 4/1999 | Kline et al. |
| 5,957,908 A | 9/1999 | Kline et al. |
| 6,004,306 A | 12/1999 | Robles et al. |
| 6,107,537 A | 8/2000 | Elder et al. |
| 6,120,487 A | 9/2000 | Ashton |
| 6,120,489 A | 9/2000 | Johnson et al. |
| 6,176,952 B1 | 1/2001 | Maugans et al. |
| 6,383,431 B1 | 5/2002 | Dobrin et al. |
| 6,383,609 B1 | 5/2002 | Annergren et al. |
| 6,409,711 B1 | 6/2002 | Jonbrink |
| 6,444,653 B1 | 9/2002 | Huppé et al. |
| 6,465,710 B1 | 10/2002 | Annergren et al. |
| 6,569,136 B1 | 5/2003 | Tao et al. |
| 6,590,136 B1 | 7/2003 | Young et al. |
| 6,605,172 B1 | 8/2003 | Anderson et al. |
| 6,686,512 B2 | 2/2004 | Herrlein et al. |
| 6,689,116 B1 | 2/2004 | Ekdahl et al. |
| 6,713,460 B2 | 3/2004 | Huppé et al. |
| 6,763,944 B2 | 7/2004 | Ronn et al. |
| 6,773,917 B1 | 8/2004 | Randall et al. |
| 6,852,517 B1 | 2/2005 | Suthers et al. |
| 6,932,800 B2 | 8/2005 | Lavon et al. |
| 6,989,006 B2 | 1/2006 | Lavon et al. |
| 7,291,139 B2 | 11/2007 | Lavon et al. |
| 7,601,145 B2 | 10/2009 | Lavon et al. |
| 7,626,073 B2 | 12/2009 | Catalan |
| 7,670,324 B2 | 3/2010 | Lavon et al. |
| 7,723,461 B1 | 5/2010 | Wagener et al. |
| 7,727,211 B2 | 6/2010 | Lavon et al. |
| 7,744,576 B2 | 6/2010 | Busam et al. |
| 7,759,393 B2 | 7/2010 | Joerger et al. |

(56) References Cited

U.S. PATENT DOCUMENTS

| | | | |
|---|---|---|---|
| 8,703,450 B2 * | 4/2014 | Bub | C12P 7/40 435/136 |
| 10,166,312 B2 * | 1/2019 | Hird | A61L 15/40 |
| 10,501,920 B2 * | 12/2019 | Hird | A61F 13/15203 |
| 2003/0199844 A1 | 10/2003 | Lavon et al. | |
| 2004/0020579 A1 | 2/2004 | Durrance et al. | |
| 2004/0024379 A1 | 2/2004 | Lavon et al. | |
| 2004/0030314 A1 | 2/2004 | Lavon et al. | |
| 2004/0039361 A1 | 2/2004 | Lavon et al. | |
| 2004/0097897 A1 | 5/2004 | Ronn et al. | |
| 2004/0142621 A1 | 7/2004 | Carroll et al. | |
| 2004/0167486 A1 | 8/2004 | Busam et al. | |
| 2004/0254555 A1 | 12/2004 | Wang et al. | |
| 2005/0003191 A1 | 1/2005 | Ehrnsperger et al. | |
| 2005/0154097 A1 | 7/2005 | Bonora | |
| 2005/0177123 A1 | 8/2005 | Catalan | |
| 2005/0203324 A1 | 9/2005 | Lee et al. | |
| 2005/0222458 A1 | 10/2005 | Cracuin et al. | |
| 2005/0222547 A1 | 10/2005 | Beruda et al. | |
| 2005/0228356 A1 | 10/2005 | Lavon et al. | |
| 2005/0239942 A1 | 10/2005 | Herfert et al. | |
| 2006/0177647 A1 | 8/2006 | Schmidt et al. | |
| 2007/0219521 A1 | 3/2007 | Hird et al. | |
| 2009/0023006 A1 | 1/2009 | Bub et al. | |
| 2010/0280218 A1 | 11/2010 | Wagener et al. | |
| 2010/0311179 A1 | 12/2010 | Coulter et al. | |
| 2011/0139657 A1 | 6/2011 | Hird et al. | |
| 2011/0139658 A1 | 6/2011 | Hird et al. | |
| 2011/0139659 A1 | 6/2011 | Hird et al. | |
| 2011/0139662 A1 | 6/2011 | Hird et al. | |

FOREIGN PATENT DOCUMENTS

| | | |
|---|---|---|
| EP | 1 102 569 B1 | 9/2003 |
| WO | WO 1990/008789 A1 | 8/1990 |
| WO | WO 1992/016565 A1 | 10/1992 |
| WO | WO 1993/005080 A1 | 3/1993 |
| WO | WO 1999/033420 A1 | 7/1999 |
| WO | WO 2000/032245 A | 6/2000 |
| WO | WO 2001/034886 A1 | 5/2001 |
| WO | WO 2001/090465 A | 11/2001 |
| WO | WO 2002/077080 A | 10/2002 |
| WO | WO 2006/092271 | 9/2006 |
| WO | WO 2007/109128 A3 | 9/2007 |

* cited by examiner

ABSORBENT ARTICLE COMPRISING A SYNTHETIC POLYMER DERIVED FROM A RENEWABLE RESOURCE AND METHODS OF PRODUCING SAID ARTICLE

CROSS REFERENCE TO RELATED APPLICATION

This application is a continuation of U.S. application Ser. No. 16/194,670, filed on Nov. 19, 2018, now issued as U.S. Pat. No. 10,501,920, which is a continuation of U.S. application Ser. No. 15/011,930, filed on Feb. 1, 2016, now issued as U.S. Pat. No. 10,166,312, which is a continuation of U.S. application Ser. No. 12/975,914, filed on Dec. 22, 2010, now abandoned, which is a continuation of U.S. application Ser. No. 11/724,341, filed on Mar. 15, 2007, now abandoned, which claims the benefit of U.S. Provisional Application No. 60/783,274, filed on Mar. 17, 2006, which is incorporated herein by reference.

FIELD OF INVENTION

The present invention relates to an absorbent article which comprises synthetic polymeric materials derived from renewable resources, where the materials have specific performance characteristics making them particularly useful in said absorbent article.

BACKGROUND OF THE INVENTION

Furthermore, many consumers display an aversion to purchasing products that are derived from petrochemicals. In some instances, consumers are hesitant to purchase products made from limited non-renewable resources such as petroleum and coal. Other consumers may have adverse perceptions about products derived from petrochemicals being "unnatural" or not environmentally friendly.

Certain alternative materials which are derived from non-petrochemical or renewable resources have been disclosed for use in absorbent articles. For example, U.S. Pat. No. 5,889,072 to Chao describes a process for preparing a cross-linked polyaspartate superabsorbent material. U.S. Pat. Nos. 6,713,460 and 6,444,653, both to Huppe et al., describe a superabsorbent material comprising glass-like polysaccharides. Furthermore, diapers having varying degrees of biodegradability have been disclosed. U.S. Pat. No. 5,783,504 to Ehret et al. describes a composite structure, which is suitable for use in diapers, comprising a nonwoven manufactured from a polymer derived from lactic acid and a film manufactured from a biodegradable aliphatic polyester polymer. PCT application WO 99/33420 discloses a superabsorbent material comprising a renewable and/or biodegradable raw material. However, these diapers and materials tend to have significantly lower performance and/or higher cost than materials derived from petrochemicals. For example, the superabsorbent materials disclosed in WO 99/33420 show a low absorption capacity under load and a low gel strength. A superabsorbent material with low gel strength tends to deform upon swelling and reduce interstitial spaces between the superabsorbent particles. This phenomenon is known as gel-blocking. Once gel-blocking occurs, further liquid uptake or distribution takes place via a very slow diffusion process. In practical terms, gel-blocking increases the susceptibility of the absorbent article to leakage.

Accordingly, it would be desirable to provide an absorbent article which comprises a polymer derived from renewable resources, where the polymer has specific performance characteristics making the polymer particularly useful in the absorbent article. Ideally, it would be desirable to provide a consumer product including a plurality of absorbent articles comprising said polymer derived from renewable resources and a communication of a related environmental message.

SUMMARY OF THE INVENTION

The present invention relates to an absorbent article having opposing longitudinal edges, the absorbent article comprising a topsheet, a backsheet joined with the topsheet, an absorbent core disposed between the topsheet and the backsheet, and a synthetic polymer derived from a first renewable resource via at least one monomeric intermediate compound. The polymer is disposed in or incorporated into one or more elements of the absorbent article. The elements are selected from a group consisting of the absorbent core, the topsheet, the backsheet, and a barrier leg cuff.

The present invention further relates to an absorbent article having a body-facing surface, and a garment-facing surface. The article comprises a topsheet, a backsheet joined with the topsheet, an absorbent core disposed between the topsheet and the backsheet, a pair of barrier cuffs, and a synthetic polyolefin. The synthetic polyolefin is derived from a first renewable resource via at least one intermediate compound. The synthetic polyolefin is either polypropylene or polyethylene. The topsheet, backsheet, or cuff substrate comprises the polyolefin.

The present invention also relates to a method for making an absorbent article comprising the steps of providing a renewable resource, deriving an intermediate monomeric compound from the renewable resource, polymerizing the monomeric compound to form a synthetic polymer, and disposing or incorporating the polymer into one or more elements of the absorbent article. The elements are selected from a group consisting of the absorbent core, the topsheet, the backsheet, and a barrier leg cuff.

DETAILED DESCRIPTION OF THE INVENTION

Figure 1A:
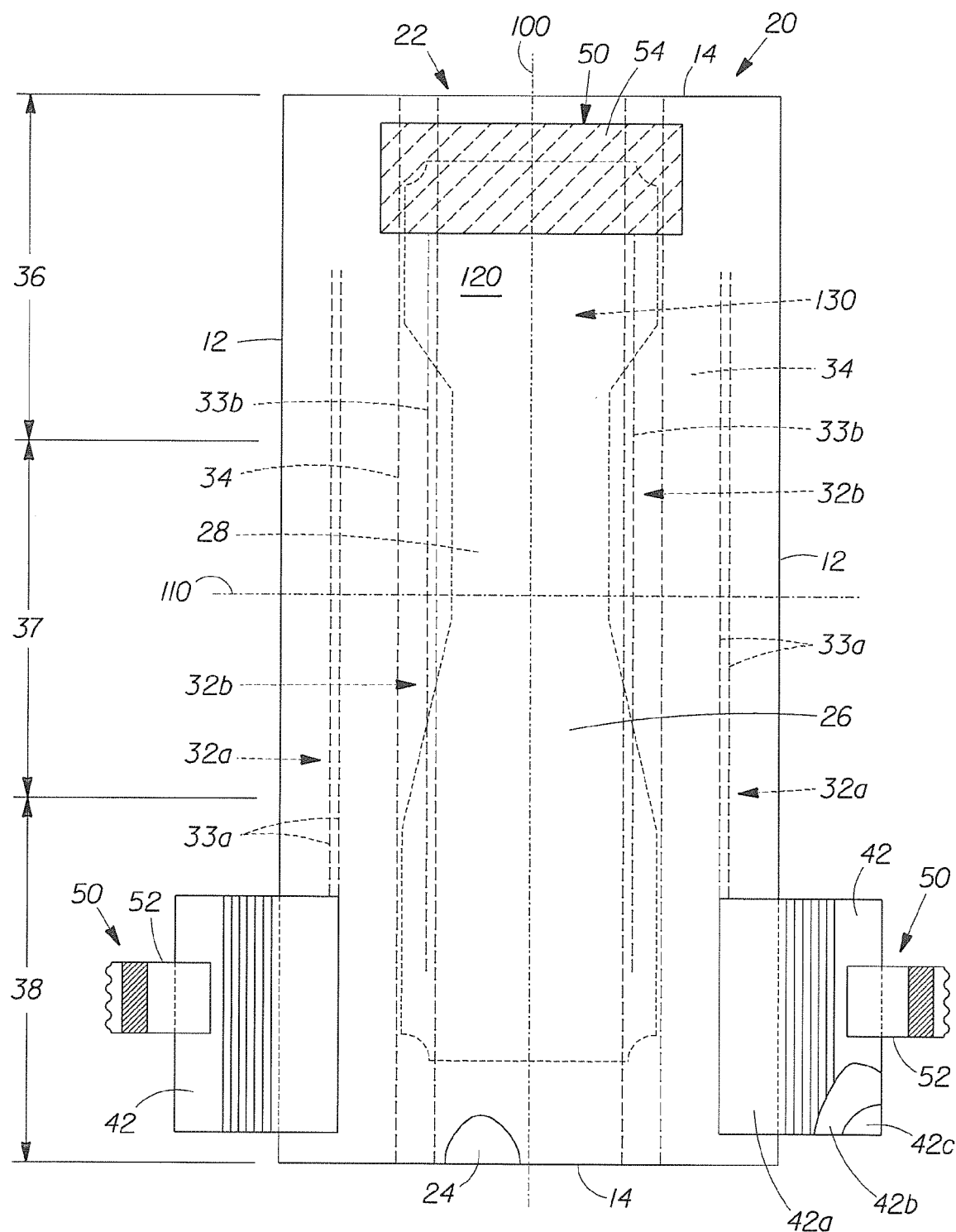
FIG. 1A is a plan view of an exemplary absorbent article in the form of a diaper in a flat, uncontracted state.

The present invention relates to an absorbent article comprising a synthetic polymer derived from a renewable resource where the polymer has specific performance characteristics. When the synthetic polymer derived from a renewable resource is in the form of a superabsorbent polymer, it exhibits an Absorption Against Pressure (AAP) value of at least about 15.0 g saline per gram polymer and/or a saline flow conductivity (SFC) of at least about $30 \times 10^{-7}$ cm³·sec/g. When the polymer is a polyolefin nonwoven suitable for use as a topsheet, it may exhibit a Liquid Strike Through value of less than about 4 seconds. When the polymer is a polyolefin nonwoven suitable for use as a barrier leg cuff, it may exhibit a hydrohead of at least about 5 mbar. When the polymer is a breathable polyolefin film suitable for use as a backsheet, it may exhibit a Moisture Vapor Transmission Rate of at least about 2000 g/m²/24 hr. When the polymer is a polyolefin film suitable for use as a backsheet, it may have an MD tensile strength of at least about 0.5 N/cm.

In another aspect, the absorbent article comprises a synthetic polymer derived from a renewable resource wherein the polymer has a $^{14}C/C$ ratio of about $1.0 \times 10^{14}$ or greater The present invention further relates to a package comprising at least one absorbent article comprising a synthetic polymer derived from a renewable resource and an overwrap securing the absorbent article(s). The absorbent article comprises a synthetic polymer derived from a renewable resource. The package may further comprise a communication of a related environmental message.

The present invention further relates to a method for making absorbent articles comprising a synthetic polymer derived from a renewable resource. The method comprises the following steps: providing a renewable resource; deriving at least one intermediate compound from the renewable resource, wherein the intermediate compound comprises a monomeric compound; polymerizing the monomeric compound to form at least one polymer, wherein the at least one polymer exhibits the requisite performance for use in an absorbent article; and incorporating the at least one polymer into an absorbent article. Additional steps, as described herein, may be incorporated into the method. Optionally the at least one polymer may be modified after the polymerization step.

I. Definitions

As used herein, the following terms shall have the meaning specified thereafter:

"Disposable" refers to items that are intended to be discarded after a limited number of uses, frequently a single use (i.e., the original absorbent article as a whole is not intended to be laundered or reused as an absorbent article, although certain materials or portions of the absorbent article may be recycled, reused, or composted). For example, certain disposable absorbent articles may be temporarily restored to substantially full functionality through the use of removable/replaceable components but the article is nevertheless considered to be disposable because the entire article is intended to be discarded after a limited number of uses.

"Absorbent article" refers to devices which absorb and contain body exudates and, more specifically, refers to devices which are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners (e.g. such as disclosed in U.S. Pat. Nos. 4,425,130; 4,687,478; 5,267,992; and 5,733,274), absorbent inserts, and the like. Absorbent articles may be disposable or may contain portions that can be reused or restored.

"Proximal" and "Distal" refer, respectively, to the location of an element relatively near to or far from the longitudinal or lateral centerline of a structure (e.g., the proximal edge of a longitudinally extending element is located nearer to the longitudinal centerline than the distal edge of the same element is located relative to the same longitudinal centerline).

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the absorbent article).

"Superabsorbent" refers to a material capable of absorbing at least ten times its dry weight of a 0.9% saline solution at 25° C. Superabsorbent polymers absorb fluid via an osmotic mechanism to form a gel, often referred to as, and used interchangeably with the term "hydrogel".

"Longitudinal" refers to a direction running substantially perpendicular from a waist edge to an opposing waist edge of the article and generally parallel to the maximum linear dimension of the article. Directions within 45 degrees of the longitudinal direction are considered to be "longitudinal"

"Lateral" refers to a direction running from a longitudinal edge to an opposing longitudinal edge of the article and generally at a right angle to the longitudinal direction. Directions within 45 degrees of the lateral direction are considered to be "lateral."

"Disposed" refers to an element being located in a particular place or position.

"Joined" refers to configurations whereby an element is directly secured to another element by affixing the element directly to the other element and to configurations whereby an element is indirectly secured to another element by affixing the element to intermediate member(s) which in turn are affixed to the other element.

"Film" refers to a sheet-like material wherein the length and width of the material far exceed the thickness of the material. Typically, films have a thickness of about 0.5 mm or less.

"Impermeable" generally refers to articles and/or elements that are not penetrative by fluid through the entire Z-directional thickness of the article under pressure of 0.14 lb/in² or less. Preferably, the impermeable article or element is not penetrative by fluid under pressures of 0.5 lb/in² or less. More preferably, the impermeable article or element is not penetrative by fluid under pressures of 1.0 lb/in² or less. The test method for determining impermeability conforms to Edana 120.1-18 or INDA IST 80.6.

"Extendibility" and "extensible" mean that the width or length of the component in a relaxed state can be extended or increased by at least about 10% without breaking or rupturing when subjected to a tensile force.

"Elastic," "elastomer," and "elastomeric" refer to a material which generally is able to extend to a strain of at least 50% without breaking or rupturing, and is able to recover substantially to its original dimensions after the deforming force has been removed.

"Elastomeric material" is a material exhibiting elastic properties. Elastomeric materials may include elastomeric films, scrims, nonwovens, and other sheet-like structures.

"Outboard" and "inboard" refer respectively to the location of an element disposed relatively far from or near to the longitudinal centerline of the diaper with respect to a second element. For example, if element A is outboard of element B, then element A is farther from the longitudinal centerline than is element B.

"Pant" refers to an absorbent article having a pre-formed waist and leg openings. A pant may be donned by inserting a wearer's legs into the leg openings and sliding the pant into position about the wearer's lower torso. Pants are also commonly referred to as "closed diapers", "prefastened diapers", "pull-on diapers", "training pants" and "diaper-pants."

"Petrochemical" refers to an organic compound derived from petroleum, natural gas, or coal.

"Petroleum" refers to crude oil and its components of paraffinic, cycloparaffinic, and aromatic hydrocarbons. Crude oil may be obtained from tar sands, bitumen fields, and oil shale.

"Renewable resource" refers to a natural resource that can be replenished within a 100 year time frame. The resource may be replenished naturally, or via agricultural techniques.

"Renewable resources" include plants, animals, fish, bacteria, fungi, and forestry products. They may be naturally occurring, hybrids, or genetically engineered organisms. Natural resources such as crude oil, coal, and peat which take longer than 100 years to form are not considered to be renewable resources "Agricultural product" refers to a renewable resource resulting from the cultivation of land (e.g. a crop) or the husbandry of animals (including fish).

"Monomeric compound" refers to an intermediate compound that may be polymerized to yield a polymer.

"Polymer" refers to a macromolecule comprising repeat units where the macromolecule has a molecular weight of at least 1000 Daltons. The polymer may be a homopolymer, copolymer, terpoymer etc. The polymer may be produced via fee-radical, condensation, anionic, cationic, Ziegler-Natta, metallocene, or ring-opening mechanisms. The polymer may be linear, branched and/or crosslinked.

"Synthetic polymer" refers to a polymer which is produced from at least one monomer by a chemical process. A synthetic polymer is not produced directly by a living organism.

"Polyethylene" and "polypropylene" refer to polymers prepared from ethylene and propylene, respectively. The polymer may be a homopolymer, or may contain up to about 10 mol % of repeat units from a co-monomer.

"Communication" refers to a medium or means by which information, teachings, or messages are transmitted.

"Related environmental message" refers to a message that conveys the benefits or advantages of the absorbent article comprising a polymer derived from a renewable resource. Such benefits include being more environmentally friendly, having reduced petroleum dependence, being derived from renewable resources, and the like.

All percentages herein are by weight unless specified otherwise.

II. Polymers Derived from Renewable Resources

A number of renewable resources contain polymers that are suitable for use in an absorbent article (i.e., the polymer is obtained from the renewable resource without intermediates). Suitable extraction and/or purification steps may be necessary, but no intermediate compound is required. Such polymers derived directly from renewable resources include cellulose (e.g. pulp fibers), starch, chitin, polypeptides, poly(lactic acid), polyhydroxyalkanoates, and the like. These polymers may be subsequently chemically modified to improve end use characteristics (e.g., conversion of cellulose to yield carboxycellulose or conversion of chitin to yield chitosan). However, in such cases, the resulting polymer is a structural analog of the starting polymer. Polymers derived directly from renewable resources (i.e., with no intermediate compounds) and their derivatives are known and these materials are not within the scope of the present invention.

The synthetic polymers of the present invention are derived from a renewable resource via an indirect route involving one or more intermediate compounds. Suitable intermediate compounds derived from renewable resources include sugars. Suitable sugars include monosaccharides, disaccharides, trisaccharides, and oligosaccharides. Sugars such as sucrose, glucose, fructose, maltose may be readily produced from renewable resources such as sugar cane and sugar beets. Sugars may also be derived (e.g., via enzymatic cleavage) from other agricultural products such as starch or cellulose. For example, glucose may be prepared on a commercial scale by enzymatic hydrolysis of corn starch. While corn is a renewable resource in North America, other common agricultural crops may be used as the base starch for conversion into glucose. Wheat, buckwheat, arracaha, potato, barley, kudzu, cassava, sorghum, sweet potato, yam, arrowroot, sago, and other like starchy fruit, seeds, or tubers are may also be used in the preparation of glucose.

Other suitable intermediate compounds derived from renewable resources include monofunctional alcohols such as methanol or ethanol and polyfunctional alcohols such as glycerol. Ethanol may be derived from many of the same renewable resources as glucose. For example, cornstarch may be enzymatically hydrolysized to yield glucose and/or other sugars. The resultant sugars can be converted into ethanol by fermentation. As with glucose production, corn is an ideal renewable resource in North America; however, other crops may be substituted. Methanol may be produced from fermentation of biomass. Glycerol is commonly derived via hydrolysis of triglycerides present in natural fats or oils, which may be obtained from renewable resources such as animals or plants.

Other intermediate compounds derived from renewable resources include organic acids (e.g., citric acid, lactic acid, alginic acid, amino acids etc.), aldehydes (e.g., acetaldehyde), and esters (e.g., cetyl palmitate, methyl stearate, methyl oleate, etc.).

Additional intermediate compounds such as methane and carbon monoxide may also be derived from renewable resources by fermentation and/or oxidation processes.

Intermediate compounds derived from renewable resources may be converted into polymers (e.g., glycerol to polyglycerol) or they may be converted into other intermediate compounds in a reaction pathway which ultimately leads to a polymer useful in an absorbent article. An intermediate compound may be capable of producing more than one secondary intermediate compound. Similarly, a specific intermediate compound may be derived from a number of different precursors, depending upon the reaction pathways utilized.

Particularly desirable intermediates include (meth)acrylic acids and their esters and salts; and olefins. In particular embodiments, the intermediate compound may be acrylic acid, ethylene, or propylene.

For example, acrylic acid is a monomeric compound that may be derived from renewable resources via a number of suitable routes. Examples of such routes are provided below.

Glycerol derived from a renewable resource (e.g., via hydrolysis of soybean oil and other triglyceride oils) may be converted into acrylic acid according to a two-step process. In a first step, the glycerol may be dehydrated to yield acrolein. A particularly suitable conversion process involves subjecting glycerol in a gaseous state to an acidic solid catalyst such as $H_3PO_4$ on an aluminum oxide carrier (which is often referred to as solid phosphoric acid) to yield acrolien. Specifics relating to dehydration of glycerol to yield acrolein are disclosed, for instance, in U.S. Pat. Nos. 2,042,224 and 5,387,720. In a second step, the acrolein is oxidized to form acrylic acid. A particularly suitable process involves a gas phase interaction of acrolein and oxygen in the presence of a metal oxide catalyst. A molybdenum and vanadium oxide catalyst may be used. Specifics relating to oxidation of acrolein to yield acrylic acid are disclosed, for instance, in U.S. Pat. No. 4,092,354.

Glucose derived from a renewable resource (e.g., via enzmatic hydrolysis of corn starch) may be converted into acrylic acid via a two step process with lactic acid as an intermediate product. In the first step, glucose may be biofermented to yield lactic acid. Any suitable microorganism capable of fermenting glucose to yield lactic acid may be used including members from the genus *Lactobacillus* such as *Lactobacillus lactis* as well as those identified in U.S. Pat. Nos. 5,464,760 and 5,252,473. In the second step, the lactic acid may be dehydrated to produce acrylic acid by use of an acidic dehydration catalyst such as an inert metal oxide carrier which has been impregnated with a phosphate salt. This acidic dehydration catalyzed method is described in further detail in U.S. Pat. No. 4,729,978. In an alternate suitable second step, the lactic acid may be converted to acrylic acid by reaction with a catalyst comprising solid aluminum phosphate. This catalyzed dehydration method is described in further detail in U.S. Pat. No. 4,786,756.

Another suitable reaction pathway for converting glucose into acrylic acid involves a two step process with 3-hydroxypropionic acid as an intermediate compound. In the first step, glucose may be biofermented to yield 3-hydroxypropionic acid. Microorganisms capable of fermenting glucose to yield 3-hydroxypropionic acid have been genetically engineered to express the requisite enzymes for the conversion. For example, a recombinant microorganism expressing the dhaB gene from *Klebsiella pneumoniae* and the gene for an aldehyde dehydrogenase has been shown to be capable of converting glucose to 3-hydroxypropionic acid. Specifics regarding the production of the recombinant organism may be found in U.S. Pat. No. 6,852,517. In the second step, the 3-hydroxypropionic acid may be dehydrated to produce acrylic acid.

Glucose derived from a renewable resource (e.g., via enzymatic hydrolysis of corn starch obtained from the renewable resource of corn) may be converted into acrylic acid by a multistep reaction pathway. Glucose may be fermented to yield ethanol. Ethanol may be dehydrated to yield ethylene. At this point, ethylene may be polymerized to form polyethylene. However, ethylene may be converted into propionaldehyde by hydroformylation of ethylene using carbon monoxide and hydrogen in the presence of a catalyst such as cobalt octacarbonyl or a rhodium complex. Propan-1-ol may be formed by catalytic hydrogenation of propionaldehyde in the presence of a catalyst such as sodium borohydride and lithium aluminum hydride. Propan-1-ol may be dehydrated in an acid catalyzed reaction to yield propylene. At this point, propylene may be polymerized to form polypropylene. However, propylene may be converted into acrolein by catalytic vapor phase oxidation. Acrolein may then be catalytically oxidized to form acrylic acid in the presence of a molybdenum-vanadium catalyst.

While the above reaction pathways yield acrylic acid, a skilled artisan will appreciate that acrylic acid may be readily converted into an ester (e.g., methyl acrylate, ethyl acrylate, etc.) or salt.

Olefins such as ethylene and propylene may also be derived from renewable resources. For example, methanol derived from fermentation of biomass may be converted to ethylene and or propylene, which are both suitable monomeric compounds, as described in U.S. Pat. Nos. 4,296,266 and 4,083,889. Ethanol derived from fermentation of a renewable resource may be converted into monomeric compound of ethylene via dehydration as described in U.S. Pat. No. 4,423,270. Similarly, propanol or isopropanol derived from a renewable resource can be dehydrated to yield the monomeric compound of propylene as exemplified in U.S. Pat. No. 5,475,183. Propanol is a major constituent of fusel oil, a by-product formed from certain amino acids when potatoes or grains are fermented to produce ethanol.

Charcoal derived from biomass can be used to create syngas (i.e., $CO+H_2$) from which hydrocarbons such as ethane and propane can be prepared (Fischer-Tropsch Process). Ethane and propane can be dehydrogenated to yield the monomeric compounds of ethylene and propylene.

III. Exemplary Synthetic Polymers

A. Superabsorbent Polymers—Certain compounds derived from renewable resources may be polymerized to yield suitable synthetic superabsorbent polymers. For example, acrylic acid derived from soybean oil via the glycerol/acrolein route described above may be polymerized under the appropriate conditions to yield a superabsorbent polymer comprising poly(acrylic acid). The absorbent polymers useful in the present invention can be formed by any polymerization and/or crosslinking techniques capable of achieving the desired properties. Typical methods for producing these polymers are described in Reissue U.S. Pat. No. 32,649 to Brandt et al.; U.S. Pat. Nos. 4,666,983, 4,625,001, 5,408,019; and published German patent application 4,020,780 to Dahmen. The processing (i.e., drying, milling, sieving, etc.) of the resulting superabsorbent polymer to yield a usable form is well known in the art.

The polymer may be prepared in the neutralized, partially neutralized, or un-neutralized form. In certain embodiments, the absorbent polymer may be formed from acrylic acid that is from about 50 mole % to about 95 mole % neutralized. The absorbent polymer may be prepared using a homogeneous solution polymerization process, or by multi-phase polymerization techniques such as inverse emulsion or suspension polymerization procedures. The polymerization reaction will generally occur in the presence of a relatively small amount of di- or poly-functional monomers such as N,N'-methylene bisacrylamide, trimethylolpropane triacrylate, ethylene glycol di(meth)acrylate, triallylamine, and methacrylate analogs of the aforementioned acrylates. The di- or poly-functional monomer compounds serve to lightly cross-link the polymer chains thereby rendering them water-insoluble, yet water-swellable.

In certain embodiments, the synthetic superabsorbent polymer comprising acrylic acid derived from renewable resources may be formed from starch-acrylic acid graft copolymers, partially neutralized starch-acrylic acid graft copolymers, crosslinked polymers of polyacrylic acid, and crosslinked polymers of partially neutralized polyacrylic acid. Preparation of these materials is disclosed in U.S. Pat. Nos. 3,661,875; 4,076,663; 4,093,776; 4,666,983; and 4,734,478.

The synthetic superabsorbent polymers particles can be surface-crosslinked after polymerization by reaction with a suitable reactive crosslinking agents. Surface-crosslinking of the initially formed superabsorbent polymers particles derived from renewable resources provides superabsorbent polymers having relatively high absorbent capacity and relatively high permeabity to fluid in the swollen state, as described below. A number of processes for introducing surface crosslinks are disclosed in the art. Suitable methods for surface crosslinking are disclosed in U.S. Pat. Nos. 4,541,871, 4,824,901, 4,789,861, 4,587,308, 4,734,478, and 5,164,459; published PCT applications WO92/16565, WO90/08789, and WO93/05080; published German patent application 4,020,780 to Dahmen; and published European patent application 509,708 to Gartner. Suitable crosslinking agents include di- or poly-functional crosslinking reagents such as di/poly-haloalkanes, di/poly-epoxides, di/poly-acid chlorides, di/poly-tosyl alkanes, di/poly-aldehydes, di/poly-alcohols, and the like.

An important characteristic of the synthetic superabsorbent polymers of the present invention is the permeability or flow conductivity of a zone or layer of the polymer particles when swollen with body fluids. This permeability or flow conductivity is defined herein in terms of the Saline Flow Conductivity (SFC) value of the superabsorbent polymer. SFC measures the ability of the swollen hydrogel zone or layer to transport or distribute body fluids under usage pressures. It is believed that when a superabsorbent polymer is present at high concentrations in an absorbent member and then swells to form a hydrogel under usage pressures, the boundaries of the hydrogel come into contact, and interstitial voids in this high-concentration region become generally bounded by hydrogel. When this occurs, it is believed the permeability or flow conductivity properties of this region are generally reflective of the permeability or flow conductivity properties of a hydrogel zone or layer formed from the superabsorbent polymer alone. It is further believed that increasing the permeability of these swollen high-concentration regions to levels that approach or even exceed conventional acquisition/distribution materials, such as wood-pulp fluff, can provide superior fluid handling properties for the absorbent member and absorbent core, thus decreasing incidents of leakage, especially at high fluid loadings. Higher SFC values also are reflective of the ability of the formed hydrogel to acquire body fluids under normal usage conditions.

The SFC value of the synthetic superabsorbent polymers derived from renewable resources useful in the present invention is at least about $30 \times 10^{-7}$ cm$^3$ sec/g. In other embodiments, the SFC value of the superabsorbent polymers useful in the present invention is at least about $50 \times 10^{-7}$ cm$^3$ sec/g. In other embodiments, the SFC value of the superabsorbent polymers useful in the present invention is at least about $100 \times 10^{-7}$ cm$^3$ sec/g. Typically, these SFC values are in the range of from about $30 \times 10^{-7}$ to about $1000 \times 10^{-7}$ cm$^3$ sec/g. However, SFC values may range from about $50 \times 10^{-7}$ to about $500 \times 10^{-7}$ cm$^3$ sec/g or from about $50 \times 10^{-7}$ to about $350 \times 10^{-7}$ cm$^3$ sec/g. A method for determining the SFC value of the superabsorbent polymers is provided hereafter in the Test Methods Section.

Another important characteristic of the superabsorbent polymers of the present invention is their ability to swell against a load. This capacity versus a load is defined in terms of the superabsorbent polymer's Absorption Against Pressure (AAP) capacity. When a superabsorbent polymer is incorporated into an absorbent member at high concentrations, the polymer needs to be capable of absorbing large quantities of body fluids in a reasonable time period under usage pressures. Usage pressures exerted on the superabsorbent polymers used within absorbent article include both mechanical pressures (e.g., exerted by the weight and motions of a wearer, taping forces, etc.) and capillary pressures (e.g., resulting from the acquisition component(s) in the absorbent core that temporarily hold fluid before it is absorbed by the superabsorbent polymer).

The AAP capacity of absorbent polymer of the useful in the present invention is generally at least about 15 g/g. In certain embodiments, the AAP capacity of absorbent polymer is generally at least about 20 g/g. Typically, AAP values range from about 15 to about 25 g/g. However, AAP values may range from about 17 to about 23 g/g or from about 20 to about 23 g/g. A method for determining the AAP capacity value of these absorbent polymers is provided hereafter in the Test Methods Section.

B. Polyolefins—Olefins derived from renewable resources may be polymerized to yield polyolefins. Ethylene derived from renewable resources may be polymerized under the appropriate conditions to prepare polyethylene having desired characteristics for use in a particular component of an absorbent article or in the packaging for said article. The polyethylene may be high density, medium density, low density, or linear-low density. Polyethylene and/or polypropylene may be produced via free-radical polymerization techniques, or by using Ziegler-Natta catalysis or Metallocene catalysts.

The polyolefin may be processed according to methods known in the art into a form suitable for the end use of the polymer. Suitable forms for polyolefins include a film, an apertured film, a microporous film, a fiber, a filament, a nonwoven, or a laminate. Suitable nonwoven forms include spunbond webs, meltblown webs, and combinations thereof (e.g., spunbond-meltblown webs (SM), spunbond-melt-blown-spunbond webs (SMS), etc.). The polyolefin may comprise mixtures or blends with other polymers such as polyolefins derived from petrochemicals. Depending on the end use and form, the polyolefin may comprise other compounds such as inorganic compounds, fillers, pigments, dyes, antioxidants, UV-stabilizers, binders, surfactants, wetting agents, and the like. For example, a polyolefin film may be impregnated with inorganic compound such as calcium carbonate, titanium dioxide, clays, silicas, zeolites, kaolin, mica, carbon, and mixtures thereof. Such compounds may serve as pore forming agents which, upon straining the film, may improve the breathability of the film. This process is described further in U.S. Pat. No. 6,605,172. A binder may be used with a polyolefin fibers, filaments, or nonwoven web. A suitable binder is a styrene-butadiene latex binder available under the trade name GENFLO™ 3160 from OMNOVA Solutions Inc.; Akron, Ohio. The resulting binder/polyolefin web may be used as an acquisition layer, which may be associated with the absorbent core. The polyolefin materials and particularly polyolefin fibers, filaments, and nonwoven webs may treated with a surfactant or wetting agent such as Irgasurf™ available from Ciba Specialty Chemicals of Tarrytown, N.Y.

Polyolefin nonwovens useful in an absorbent article may have a basis weight between about 1 g/m$^2$ and about 50 g/m$^2$ or between about 5 g/m$^2$ and about 30 g/m$^2$, as measured according to the Basis Weight Test provided below. Polyolefin nonwovens suitable for use as a topsheet may have an average liquid strike-through time of less than about 4 seconds, as measured according to the Liquid Strike-Through Test provided below. In other embodiments the polyolefin nonwoven may have an average strike-through time of less than about 3 seconds or less than about 2 seconds.

Polyolefin nonwoven useful as a barrier leg cuff may have a hydrohead of greater than about 5 mbar or about 6 mbar and less than about 10 mbar or about 8 mbar, as measured according to the Hydrohead test provided below.

Polyolefin films suitable for use as a backsheet may have an MD tensile strength of greater than about 0.5 N/cm or about 1 N/cm and less than about 6 N/cm or about 5 N/cm, as measured according to the Tensile Test as provided below. For breathable polyolefin films suitable for use as a backsheet, the film may have a Moisture Vapor Transmission Rate (MVTR) of at least about 2000 g/m$^2$/hr, preferably greater than about 2400 g/m$^2$/hr, and even more preferably, greater than about 3000 g/m$^2$/hr, as measured by the Moisture Vapor Transmission Rate test provided below. It should be recognized that non-breathable backsheets, which are also useful in diapers, would exhibit an MVTR value of about 0 g/m$^2$/hr.

C. Other Polymers—It should be recognized that any of the aforementioned synthetic polymers may be formed by using a combination of monomers derived from renewable resources and monomers derived from non-renewable (e.g., petroleum) resources. For example, the superabsorbent polymer of poly(acrylic acid) may be polymerized from a combination of acrylic acid derived form renewable resources and acrylic acid derived from non-renewable resources. The monomer derived from a renewable resource may comprise at least about 5% by weight [weight of renewable resource monomer/weight of resulting polymer× 100], at least about 10% by weight, at least about 20% by weight, at least about 30% by weight, at least about 40% by weight, or at least about 50% by weight of the superabsorbent polymer.

IV. Absorbent Articles Comprising the Synthetic Polymer Derived from Renewable Resources The present invention relates to an absorbent article comprising a synthetic polymer derived from a renewable resource. The polymer has specific performance characteristics. The polymers derived from a renewable resource may be in any suitable form such as a film, nonwoven, superabsorbent, and the like.

Figure 1B:
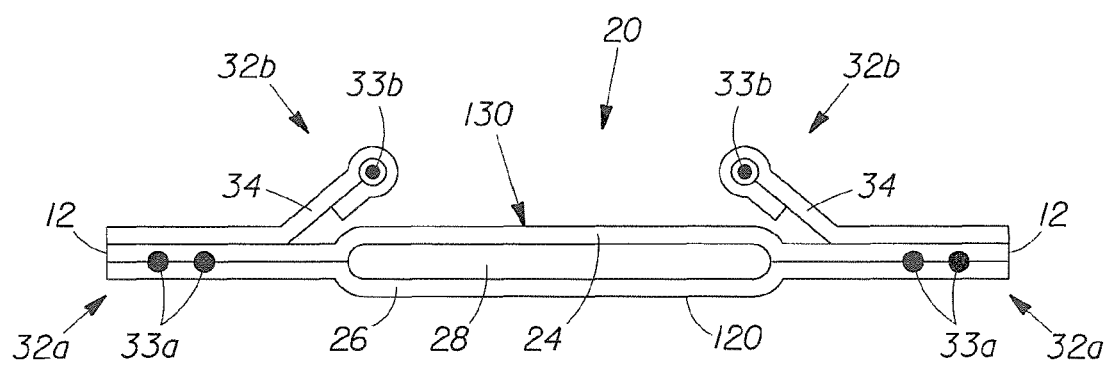
FIG. 1B is a cross-sectional view of the diaper of FIG. 1A taken along the lateral centerline.

FIG. 1A is a plan view of an exemplary, non-limiting embodiment of an absorbent article in the form of a diaper 20 in a flat, uncontracted state (i.e., without elastic induced contraction). The garment-facing surface 120 of the diaper 20 is facing the viewer and the body-facing surface 130 is opposite the viewer. The diaper 20 includes a longitudinal centerline 100 and a lateral centerline 110. FIG. 1B is a cross-sectional view of the diaper 20 of FIG. 1A taken along the lateral centerline 110. The diaper 20 may comprise a chassis 22. The diaper 20 and chassis 22 are shown to have a front waist region 36, a rear waist region 38 opposed to the front waist region 36, and a crotch region 37 located between the front waist region 36 and the rear waist region 38. The waist regions 36 and 38 generally comprise those portions of the diaper 20 which, when worn, encircle the waist of the wearer. The waist regions 36 and 38 may include elastic elements such that they gather about the waist of the wearer to provide improved fit and containment. The crotch region 37 is that portion of the diaper 20 which, when the diaper 20 is worn, is generally positioned between the legs of the wearer.

The outer periphery of diaper 20 and/or chassis 22 is defined by longitudinal edges 12 and lateral edges 14. The chassis 22 may have opposing longitudinal edges 12 that are oriented generally parallel to the longitudinal centerline 100. However, for better fit, longitudinal edges 12 may be curved or angled to produce, for example, an "hourglass" shape diaper when viewed in a plan view. The chassis 22 may have opposing lateral edges 14 that are oriented generally parallel to the lateral centerline 110.

The chassis 22 may comprises a liquid permeable topsheet 24, a backsheet 26, and an absorbent core 28 between the topsheet 24 and the backsheet 26. The absorbent core 28 may have a body-facing surface and a garment facing-surface. The topsheet 24 may be joined to the core 28 and/or the backsheet 26. The backsheet 26 may be joined to the core 28 and/or the topsheet 24. It should be recognized that other structures, elements, or substrates may be positioned between the core 28 and the topsheet 24 and/or backsheet 26. In certain embodiments, the chassis 22 comprises the main structure of the diaper 20 and other features may added to form the composite diaper structure. The topsheet 24, the backsheet 26, and the absorbent core 28 may be assembled in a variety of well-known configurations as described generally in U.S. Pat. Nos. 3,860,003; 5,151,092; 5,221,274; 5,554,145; 5,569,234; 5,580,411; and 6,004,306.

The absorbent core 28 may comprise the superabsorbent polymer derived from a renewable resource of the present invention as well as a wide variety of other liquid-absorbent materials commonly used in diapers and other absorbent articles. Examples of suitable absorbent materials include comminuted wood pulp, which is generally referred to as air felt; chemically stiffened, modified or cross-linked cellulosic fibers; superabsorbent polymers or absorbent gelling materials; melt blown polymers, including co-form, biosoluble vitreous microfibers; tissue, including tissue wraps and tissue laminates; absorbent foams; absorbent sponges; and any other known absorbent material or combinations of materials. Exemplary absorbent structures for use as the absorbent core 28 are described in U.S. Pat. Nos. 4,610,678; 4,673,402; 4,834,735; 4,888,231; 5,137,537; 5,147,345; 5,342,338; 5,260,345; 5,387,207; 5,397,316; 5,625,222; and 6,932,800. Further exemplary absorbent structures may include non-removable absorbent core components and removable absorbent core components. Such structures are described in U.S. Publication 2004/0039361A1; 2004/0024379A1; 2004/0030314A1; 2003/0199844A1; and 2005/0228356A1. Ideally, the absorbent core 28 may be comprised entirely of materials derived from renewable resources; however, the absorbent core 28 may comprise materials derived from non-renewable resources.

The absorbent core 28 may comprise a fluid acquisition component, a fluid distribution component, and a fluid storage component. A suitable absorbent core 28 comprising an acquisition layer, a distribution layer, and a storage layer is described in U.S. Pat. No. 6,590,136.

Another suitable absorbent core construction where the superabsorbent polymer of the present invention may be used is described in U.S. Publication No. 2004/0167486 to Busam et al. The absorbent core of the aforementioned publication uses no or, in the alternative, minimal amounts of absorbent fibrous material within the core. Generally, the absorbent core may include no more than about 20% weight percent of absorbent fibrous material (i.e., [weight of fibrous material/total weight of the absorbent core]×100).

The topsheet 24 is generally a portion of the diaper 20 that may be positioned at least in partial contact or close proximity to a wearer. Suitable topsheets 24 may be manufactured from a wide range of materials such as woven or nonwoven webs of natural fibers (e.g., wood or cotton fibers), synthetic fibers (e.g., polyester or polypropylene fibers), or a combination of natural and synthetic fibers; apertured plastic films; porous foams or reticulated foams. The topsheet 24 is generally supple, soft feeling, and non-irritating to a wearer's skin. Generally, at least a portion of the topsheet 24 is liquid pervious, permitting liquid to readily penetrate through the thickness of the topsheet 24. Suitably, the topsheet 24 comprises a polymer (e.g. polyethylene) derived from a renewable resource. Alternately, a suitable topsheet 24 is available from BBA Fiberweb, Brentwood, Tenn. as supplier code 055SLPV09U.

Any portion of the topsheet 24 may be coated with a lotion as is known in the art. Examples of suitable lotions include those described in U.S. Pat. Nos. 5,607,760; 5,609,587; 5,635,191; and 5,643,588. The topsheet 24 may be fully or partially elasticized or may be foreshortened so as to provide a void space between the topsheet 24 and the core 28. Exemplary structures including elasticized or foreshortened topsheets are described in more detail in U.S. Pat. Nos. 4,892,536; 4,990,147; 5,037,416; and 5,269,775.

The backsheet 26 is generally positioned such that it may be at least a portion of the garment-facing surface 120 of the diaper 20. Backsheet 26 may be designed to prevent the exudates absorbed by and contained within the diaper 20 from soiling articles that may contact the diaper 20, such as bed sheets and undergarments. In certain embodiments, the backsheet 26 is substantially water-impermeable; however, the backsheet 26 may be made breathable so as to permit vapors to escape while preventing liquid exudates from escaping. The polyethylene film may be made breathable by inclusion of inorganic particulate material and subsequent tensioning of the film. Breathable backsheets may include materials such as woven webs, nonwoven webs, composite materials such as film-coated nonwoven webs, and microporous films. Suitably, the backsheet 26 comprises a polymer such (e.g. polyethylene) derived from a renewable resource as disclosed above. Alternative backsheets 26 derived from non-renewable resources include films manufactured by Tredegar Industries Inc. of Terre Haute, Ind. and sold under the trade names X15306, X10962, and X10964; and microporous films such as manufactured by Mitsui Toatsu Co., of Japan under the designation ESPOIR NO and by EXXON Chemical Co., of Bay City, Tex., under the designation EXXAIRE. Other alternative breathable backsheets 26 are described in U.S. Pat. Nos. 5,865,823, 5,571,096, and 6,107,537.

Backsheet 26 may also consist of more than one layer. For example, the backsheet 26 may comprise an outer cover and an inner layer or may comprise two outer layers with an inner layer disposed therebetween. The outer cover may have longitudinal edges and the inner layer may have longitudinal edges. The outer cover may be made of a soft, non-woven material. The inner layer may be made of a substantially water-impermeable film. The outer cover and an inner layer may be joined together by adhesive or any other suitable material or method. Suitably, the nonwoven outer cover and the water-impermeable film comprise polymers (e.g., polyethylene) may be derived from renewable resources. Alternatively, a suitable outer cover and inner layer derived from non-renewable resources are available, respectively, as supplier code A18AH0 from Corovin GmbH, Peine, Germany and as supplier code PGBR4WPR from RKW Gronau GmbH, Gronau, Germany. While a variety of backsheet configurations are contemplated herein, it would be obvious to those skilled in the art that various other changes and modifications can be made without departing from the spirit and scope of the invention.

The diaper 20 may include a fastening system 50. When fastened, the fastening system 50 interconnects the front waist region 36 and the rear waist region 38. When fastened, the diaper 20 contains a circumscribing waist opening and two circumscribing leg openings. The fastening system 50 may comprise an engaging member 52 and a receiving member 54. The engaging member 52 may comprise hooks, loops, an adhesive, a cohesive, a tab, or other fastening mechanism. The receiving member 54 may comprise hooks, loops, a slot, an adhesive, a cohesive, or other fastening mechanism that can receive the engaging member 52. Suitable engaging member 52 and receiving member 54 combinations are well known in the art and include but are not limited to hooks/loop, hooks/hooks, adhesive/polymeric film, cohesive/cohesive, adhesive/adhesive, tab/slot, and button/button hole. Suitably, the fastening system 50 may comprise a polymer (e.g., polyethylene film or a polyethylene nonwoven) derived from a renewable resource.

The diaper 20 may include front ears (not shown) and/or back ears 42. The front and/or back ears 42 may be unitary elements of the diaper 20 (i.e., they are not separately manipulative elements secured to the diaper 20, but rather are formed from and are extensions of one or more of the various layers of the diaper). In certain embodiments, the front and/or back ears 42 may be discrete elements that are joined to the chassis 22, as shown in FIG. 1A. Discrete front and/or back ears 42 may be joined to the chassis 22 by any bonding method known in the art such as adhesive bonding, pressure bonding, heat bonding, and the like. In other embodiments, the front and/or back ears 42 may comprise a discrete element joined to the chassis 22 with the chassis 22 having a layer, element, or substrate that extends over the front and/or back ear 42. The front ears and back ears 42 may be extensible, inextensible, elastic, or inelastic. The front ears and back ears 42 may be formed from nonwoven webs, woven webs, knitted fabrics, polymeric and elastomeric films, apertured films, sponges, foams, scrims, and combinations and laminates thereof. In certain embodiments the front ears and back ears 42 may be formed of a stretch laminate comprising a first nonwoven 42a, elastomeric material 42b, and, optionally, a second nonwoven 42c or other like laminates. The first and second nonwoven 42a, 42c may comprise a synthetic polymer (e.g., polyethylene) derived from a renewable resource. A suitable elastomeric material 42b may comprise a natural elastomer such as natural rubber or may comprise a synthetic elastomer such as the elastomeric film available from Tredegar Corp, Richmond, Va., as supplier code X25007. An alternate stretch laminate may be formed from the Tredegar X25007 elastomer disposed between two nonwoven layers (available from BBA Fiberweb, Brentwood, Tenn. as supplier code FPN332).

The diaper 20 may further include leg cuffs 32a, 32b which provide improved containment of liquids and other body exudates. Leg cuffs 32a, 32b may also be referred to as gasketing cuffs, outer leg cuffs, leg bands, side flaps, elastic cuffs, barrier cuffs, second cuffs, inner leg cuffs, or "stand-up" elasticized flaps. U.S. Pat. No. 3,860,003 describes a disposable diaper which provides a contractible leg opening having a side flap and one or more elastic members to provide an elasticized leg cuff (i.e., a gasketing cuff). U.S. Pat. Nos. 4,808,178 and 4,909,803 describe disposable diapers having "stand-up" elasticized flaps (i.e., barrier cuffs) which improve the containment of the leg regions. U.S. Pat. Nos. 4,695,278 and 4,795,454 describe disposable diapers having dual cuffs, including gasketing cuffs and barrier cuffs.

FIGS. 1A-B shows the diaper 20 having dual cuffs: gasketing cuff 32a and barrier cuff 32b. The barrier cuff 32b may include one or more barrier elastic members 33b. The barrier elastic members 33b may be joined to a barrier cuff substrate 34. The barrier cuff substrate 34 may comprise a polymer derived from a renewable resource. In certain embodiments, the barrier cuff substrate 34 may be a polymeric film or nonwoven. The barrier cuff 32b may be disposed on the body-facing surface of the chassis 22. The barrier cuff substrate 34 may extend laterally from the longitudinal edge 12 of the chassis 22 to a point inboard of the longitudinal edge 122. The barrier cuff 32b generally extends longitudinally at least through the crotch region 37. The barrier elastic members 33b allow a portion of the barrier cuff 32b to be spaced away from the body-facing surface of the diaper 20.

The gasketing cuff 32a may include one or more gasketing elastic members 33a. The gasketing elastic member 33a may be joined to one or more of the existing elements or substrates of the diaper 20 (e.g., topsheet 24, backsheet 26, barrier cuff substrate 34, etc.). In some embodiments, it may be desirable to treat all or a portion of the leg cuffs 32 with a hydrophilic surface coasting such as is described in U.S. Patent Publication 2005/0177123A1. Suitable gasketing and barrier elastic members 33a, 33b include natural rubber, synthetic rubbers, and other elastomers.

In other suitable embodiments, the diaper 20 may be preformed by the manufacturer to create a pant. A pant may be preformed by any suitable technique including, but not limited to, joining together portions of the article using refastenable and/or non-refastenable bonds (e.g., seam, weld, adhesive, cohesive bond, fastener, etc.). For example, the diaper 20 of FIG. 1A may be manufactured with the fastening system 50 engaged (i.e., the engaging member 52 is joined to the receiving member 54). As an additional example, the diaper 20 of FIG. 1A may be manufactured with the front ears 40 joined to the back ears 42 by way of a bond such as an adhesive bond, a mechanical bond, or some other bonding technique known in the art. Suitable pants are disclosed in U.S. Pat. Nos. 5,246,433; 5,569,234; 6,120,487; 6,120,489; 4,940,464; 5,092,861; 5,897,545; and 5,957,908.

V. Providing the Absorbent Article to a Consumer

Figure 2A:
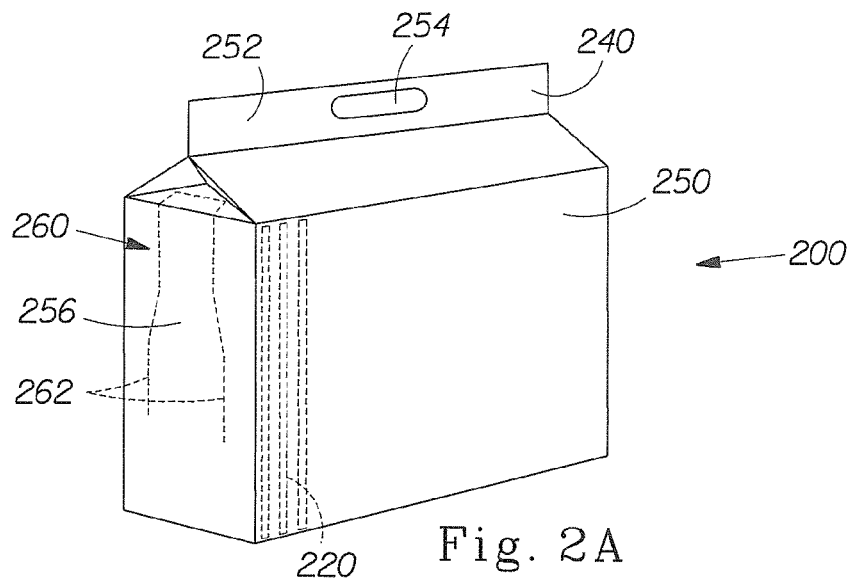
FIGS. 2A-B are perspective views of a package comprising an absorbent article.
Figure 2B:
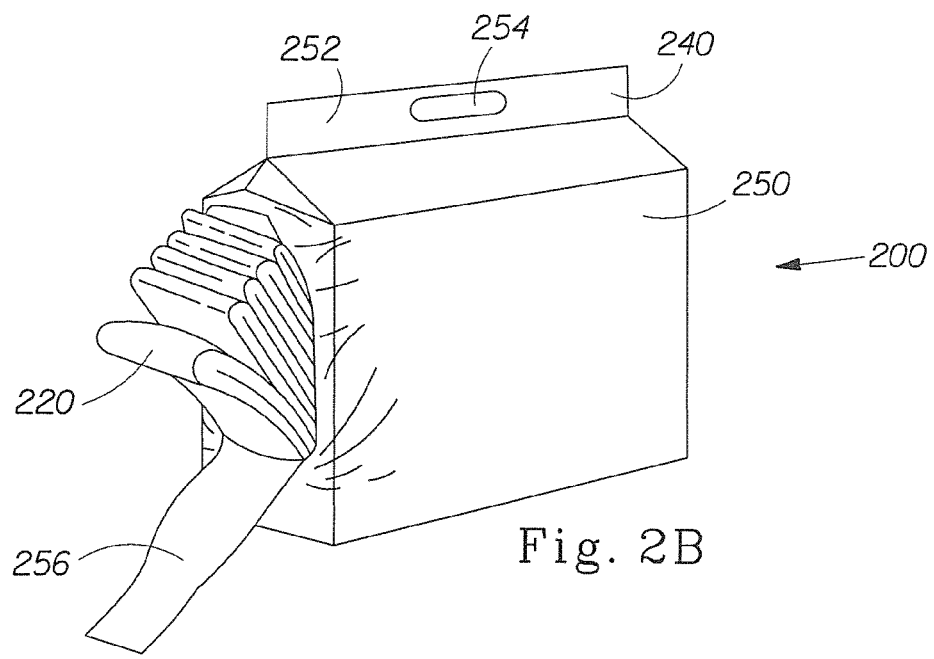

One or more absorbent articles (e.g., diapers) 220 may be provided as a package 200, as shown in FIGS. 2A-B. Generally, the package 200 allows for a quantity of absorbent articles 220 to be delivered to and purchased by a consumer while economizing space and simplifying transport and storage. The package 200 includes at least one absorbent article 220 secured by an overwrap 250. The overwrap 250 may partially or fully cover the absorbent article(s), which may be compressed or uncompressed. FIG. 2A depicts an overwrap 250 that completely covers and encases a plurality of absorbent articles 220. The overwrap 250 may comprise a variety of materials including, but not limited to, thermoplastic films, nonwovens, wovens, foils, fabrics, papers, cardboard, elastics, cords, straps, and combinations thereof. Other suitable package structures and overwraps are described in U.S. Pat. Nos. 4,846,587; 4,934,535; 4,966,286; 5,036,978; 5,050,742; and 5,054,619. In certain embodiments, the overwrap 250 comprises a synthetic polymer (e.g., a polyolefin) derived form a renewable resource. While the package 200 is not limited in shape, it may be desirable for the package 200 to have the shape of a parallelepiped or substantially similar to a parallelepiped (e.g., a solid at least a substantially planar base and four substantially planar sides). Such a shape is ideal for packaging, stacking, and transport. The package 200 is not limited in size; however, in certain embodiments, the size of the package 200 should be no greater than is required to contain the absorbent articles 220.

The package 200 may have a handle 240. In certain embodiments, the handle 240 may be a discrete element such as a strap that may be affixed to the overwrap 250. In the embodiment shown in FIGS. 2A-B, the handle 240 is integral to the overwrap 250. For this embodiment, the handle 240 may comprise an extension 252 from the overwrap 250. The extension 252 may have an aperture 254 there through. The aperture 254 ideally sized to permit entry by one or more digits of an adult hand.

An opening device 260 may be provided in the overwrap 250. For example, the opening device 260 may comprise a line of weakness 262 (e.g., perforations) in an overwrap 250 made from paper, cardboard, or film. The opening device 260 allows for partial or full removal of a flap 256 which is a portion of the overwrap 250. Partial of full removal of the flap 256 may allow for improved access to the absorbent articles 220. The opening device 260 and flap 256 are shown in a closed configuration in FIG. 2A and in an open configuration in FIG. 2B. An exemplary opening device 260 is presented in U.S. Pat. No. 5,036,978.

The package 200 may contain multiple overwraps 250. For example, a plurality of absorbent articles may be secured with a first overwrap such as a thermoplastic film and then a plurality of film wrapped absorbent articles may be secured in a second overwrap such as a cardboard box or another thermoplastic film.

VI. Communicating a Related Environmental Message a Consumer

The present invention may further comprise a related environmental message or may further comprise a step of communicating a related environmental message to a consumer. The related environmental message may convey the benefits or advantages of the absorbent article comprising a polymer derived from a renewable resource. The related environmental message may identify the absorbent articles as: being environmentally friendly or Earth friendly; having reduced petroleum (or oil) dependence or content; having reduced foreign petroleum (or oil) dependence or content; having reduced petrochemicals or having components that are petrochemical free; and/or being made from renewable resources or having components made from renewable resources. This communication is of importance to consumers that may have an aversion to petrochemical use (e.g., consumers concerned about depletion of natural resources or consumers who find petrochemical based products unnatural or not environmentally friendly) and to consumers that are environmentally conscious. Without such a communication, the benefit of the present invention may be lost on some consumers.

The communication may be effected in a variety of communication forms. Suitable communication forms include store displays, posters, billboard, computer programs, brochures, package literature, shelf information, videos, advertisements, internet web sites, pictograms, iconography, or any other suitable form of communication. The information could be available at stores, on television, in a computer-accessible form, in advertisements, or any other appropriate venue. Ideally, multiple communication forms may be employed to disseminate the related environmental message.

The communication may be written, spoken, or delivered by way of one or more pictures, graphics, or icons. For example, a television or internet based-advertisement may have narration, a voice-over, or other audible conveyance of the related environmental message. Likewise, the related environmental message may be conveyed in a written form using any of the suitable communication forms listed above. In certain embodiments, it may be desirable to quantify the reduction of petrochemical usage of the present absorbent article compared to absorbent articles that are presently commercially available.

Figure 3A:
FIGS. 3A-F are illustrations of several suitable embodiments of icons communicating reduced petrochemical dependence and/or environmental friendliness.
Figure 3B:
Figure 3C:
Figure 3D:
Figure 3E:
Figure 3F:
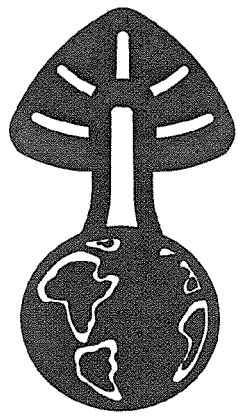

In other embodiments, the communication form may be one or more icons. FIGS. 3A-F depict several suitable embodiments of a communication in the form of icon 310. One or more icons 310 may be used to convey the related environmental message of reduced petrochemical usage. Suitable icons 310 communicating the related environmental message of reduced petroleum usage are shown in FIGS. 3A-B. Icons communicating the related environmental message of environmental friendliness or renewable resource usage are shown in FIGS. 3C-F. In certain embodiments, the icons 310 may be located on the package 200 (as shown in FIGS. 2A-B) containing the absorbent articles, on the absorbent article, on an insert adjoining the package or the articles, or in combination with any of the other forms of the communication listed above.

The related environmental message may also include a message of petrochemical equivalence. As presented in the Background, many renewable, naturally occurring, or non-petroleum derived polymers have been disclosed. However, these polymers often lack the performance characteristics that consumers have come to expect when used in absorbent articles. Therefore, a message of petroleum equivalence may be necessary to educate consumers that the polymers derived from renewable resources, as described above, exhibit equivalent or better performance characteristics as compared to petroleum derived polymers. A suitable petrochemical equivalence message can include comparison to an absorbent article that does not have a polymer derived from a renewable resource. For example, a suitable combined message may be, "Diaper Brand A with an environmentally friendly absorbent material is just as absorbent as Diaper Brand B." This message conveys both the related environmental message and the message of petrochemical equivalence.

VII. Method of Making an Absorbent Article Having a Polymer Derived from a Renewable Resource The present invention further relates to a method for making an absorbent article comprising a superabsorbent polymer derived from a renewable resource. The method comprises the steps of providing a renewable resource; deriving a monomer from the renewable resource; polymerizing the monomer to form a synthetic superabsorbent polymer having a Saline Flow Conductivity value of at least about $30 \times 10^{-7}$ cm$^3 \cdot$sec/g and an Absorption Against Pressure value of at least about 15 g/g; and incorporating said superabsorbent polymer into an absorbent article. The present invention further relates to providing one or more of the absorbent articles to a consumer and communicating reduced petrochemical usage to the consumer. The polymer derived from renewable resources may undergo additional process steps prior to incorporation into the absorbent article. Such process steps include drying, sieving, surface crosslinking, and the like.

The present invention further relates to a method for making an absorbent article comprising a synthetic polyolefin derived from a renewable resource. The method comprises the steps of providing a renewable resource; deriving an olefin monomer from the renewable resource; polymerizing the monomer to form a synthetic polyolefin having a $^{14}$C/C ratio of about $1.0 \times 10^{-14}$ or greater; and incorporating said polyolefin into an absorbent article. The synthetic polyolefin exhibits one or more of the above referenced performance characteristics. The present invention further relates to providing one or more of the absorbent articles to a consumer and communicating reduced petrochemical usage to the consumer. The polymer derived from renewable resources may undergo additional process steps prior to incorporation into the absorbent article. Such process steps include, film formation, fiber formation, ring rolling, and the like.

VIII. Validation of Polymers Derived from Renewable Resources

A suitable validation technique is through $^{14}$C analysis. A common analysis technique in carbon-14 dating is measuring the ratio of $^{14}$C to total carbon within a sample ($^{14}$C/C). Research has noted that fossil fuels and petrochemicals generally have a $^{14}$C/C ratio of less than about $1 \times 10^{-15}$. However, polymers derived entirely from renewable resources typically have a $^{14}$C/C ratio of about $1.2 \times 10^{-12}$. When compared, the polymers derived from renewable resources may have a $^{14}$C/C ratio three orders of magnitude ($10^3 = 1,000$) greater than the $^{14}$C/C ratio of polymers derived from petrochemicals. Polymers useful in the present invention have a $^{14}$C/C ratio of about $1.0 \times 10^{-14}$ or greater. In other embodiments, the petrochemical equivalent polymers of the present invention may have a $^{14}$C/C ratio of about $1.0 \times 10^{-13}$ or greater or a $^{14}$C/C ratio of about $1.0 \times 10^{-12}$ or greater. Suitable techniques for $^{14}$C analysis are known in the art and include accelerator mass spectrometry, liquid scintillation counting, and isotope mass spectrometry. These techniques are described in U.S. Pat. Nos. 3,885,155, 4,427,884, 4,973,841, 5,438,194, and 5,661,299.

IX. Test Methods

Saline Flow Conductivity

The method to determine the permeability of a swollen hydrogel layer 718 is the "Saline Flow Conductivity" also known as "Gel Layer Permeability" and is described in several references, including, EP A 640 330, filed on Dec. 1, 1993, U.S. Ser. No. 11/349,696, filed on Feb. 3, 2004, U.S. Ser. No. 11/347,406, filed on Feb. 3, 2006, U.S. Ser. No. 06/682,483, filed on Sep. 30, 1982, and U.S. Pat. No. 4,469,710, filed on Oct. 14, 1982. The equipment used for this method is described below.

Permeability Measurement System

Figure 4:
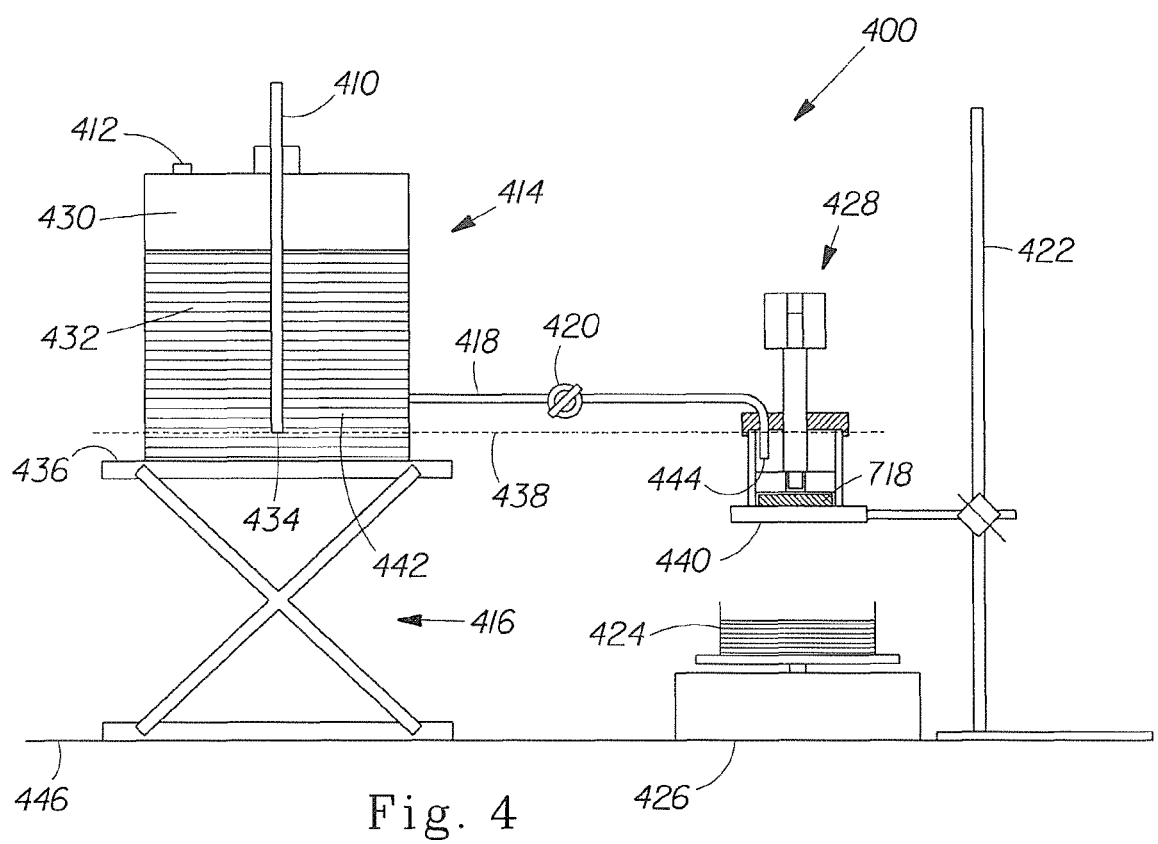
FIG. 4 is a partial cross-sectional side view of a suitable permeability measurement system for conducting the Saline Flow Conductivity Test.

FIG. 4 shows permeability measurement system 400 set-up with the constant hydrostatic head reservoir 414, open-ended tube for air admittance 410, stoppered vent for refilling 412, laboratory jack 416, delivery tube 418, stopcock 420, ring stand support 422, receiving vessel 424, balance 426 and piston/cylinder assembly 428.

Figure 5:
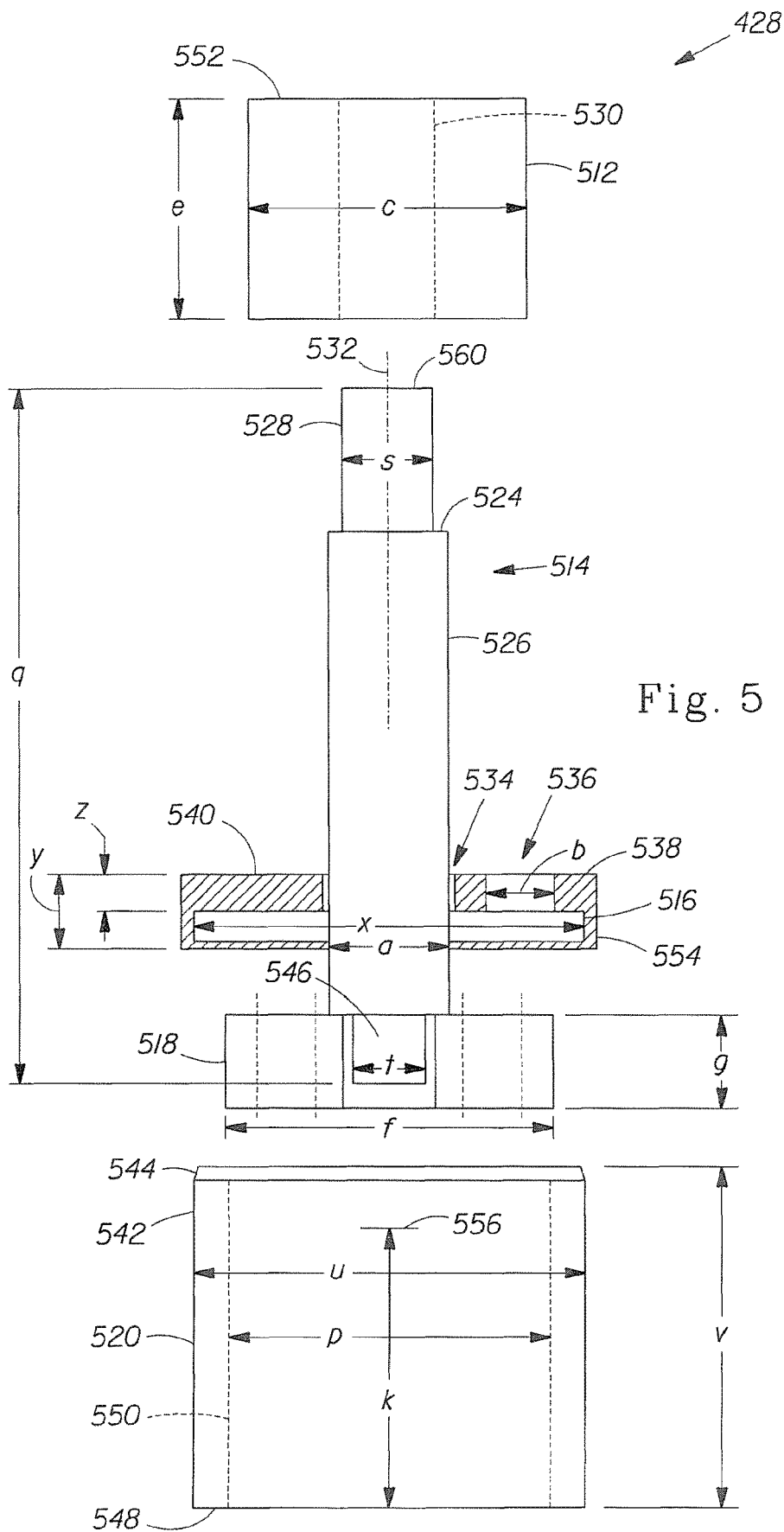
FIG. 5 is a cross-sectional side view of a piston/cylinder assembly for use in conducting the Saline Flow Conductivity Test.
Figure 6:
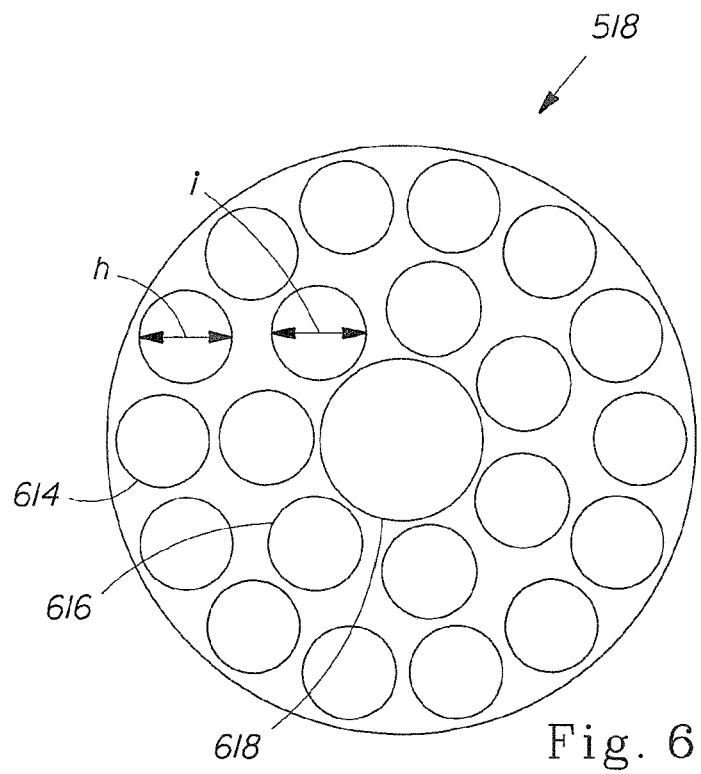
FIG. 6 is a top view of a piston head suitable for use in the piston/cylinder assembly shown in FIG. 5.

FIG. 5 shows the piston/cylinder assembly 428 comprising a metal weight 512, piston shaft 514, piston head 518, lid 516, and cylinder 520. The cylinder 520 is made of transparent polycarbonate (e.g., Lexan®) and has an inner diameter p of 6.00 cm (area=28.27 cm$^2$) with inner cylinder walls 550 which are smooth. The bottom 548 of the cylinder 520 is faced with a US. Standard 400 mesh stainless-steel screen cloth (not shown) that is bi-axially stretched to tautness prior to attachment to the bottom 548 of the cylinder 520. The piston shaft 514 is made of transparent polycarbonate (e.g., Lexan®) and has an overall length q of approximately 127 mm. A middle portion 526 of the piston shaft 514 has a diameter r of 21.15 mm. An upper portion 528 of the piston shaft 514 has a diameter s of 15.8 mm, forming a shoulder 524. A lower portion 546 of the piston shaft 514 has a diameter t of approximately ⅝ inch and is threaded to screw firmly into the center hole 618 (see FIG. 6) of the piston head 518. The piston head 518 is perforated, made of transparent polycarbonate (e.g., Lexan®), and is also screened with a stretched US. Standard 400 mesh stainless-steel screen cloth (not shown). The weight 512 is stainless steel, has a center bore 530, slides onto the upper portion 528 of piston shaft 514 and rests on the shoulder 524. The combined weight of the piston head 518, piston shaft 514 and weight 512 is 596 g (±6 g), which corresponds to 0.30 psi over the area of the cylinder 520. The combined weight may be adjusted by drilling a blind hole down a central axis 532 of the piston shaft 514 to remove material and/or provide a cavity to add weight. The cylinder lid 516 has a first lid opening 534 in its center for vertically aligning the piston shaft 514 and a second lid opening 536 near the edge 538 for introducing fluid from the constant hydrostatic head reservoir 414 into the cylinder 520.

A first linear index mark (not shown) is scribed radially along the upper surface 552 of the weight 512, the first linear index mark being transverse to the central axis 532 of the piston shaft 514. A corresponding second linear index mark (not shown) is scribed radially along the top surface 560 of the piston shaft 514, the second linear index mark being transverse to the central axis 532 of the piston shaft 514. A corresponding third linear index mark (not shown) is scribed along the middle portion 526 of the piston shaft 514, the third linear index mark being parallel with the central axis 532 of the piston shaft 514. A corresponding fourth linear index mark (not shown) is scribed radially along the upper surface 540 of the cylinder lid 516, the fourth linear index mark being transverse to the central axis 532 of the piston shaft 514. Further, a corresponding fifth linear index mark (not shown) is scribed along a lip 554 of the cylinder lid 516, the fifth linear index mark being parallel with the central axis 532 of the piston shaft 514. A corresponding sixth linear index mark (not shown) is scribed along the outer cylinder wall 542, the sixth linear index mark being parallel with the central axis 532 of the piston shaft 514. Alignment of the first, second, third, fourth, fifth, and sixth linear index marks allows for the weight 512, piston shaft 514, cylinder lid 516, and cylinder 520 to be re-positioned with the same orientation relative to one another for each measurement.

The cylinder 520 specification details are:
Outer diameter u of the Cylinder 520: 70.35 mm
Inner diameter p of the Cylinder 520: 60.0 mm
Height v of the Cylinder 520: 60.5 mm
The cylinder lid 516 specification details are:
Outer diameter w of cylinder lid 516: 76.05 mm
Inner diameter x of cylinder lid 516: 70.5 mm
Thickness y of cylinder lid 516 including lip 554: 12.7 mm
Thickness z of cylinder lid 516 without lip: 6.35 mm
Diameter a of first lid opening 534: 22.25 mm
Diameter b of second lid opening 536: 12.7 mm
Distance between centers of first and second lid openings 534 and 536: 23.5 mm
The weight 512 specification details are:
Outer diameter c: 50.0 mm
Diameter d of center bore 530: 16.0 mm
Height e: 39.0 mm
The piston head 518 specification details are
Diameter f: 59.7 mm
Height g: 16.5 mm
Outer holes 614 (14 total) with a 9.65 mm diameter h, outer holes 614 equally spaced with centers being 47.8 mm from the center of center hole 618
Inner holes 616 (7 total) with a 9.65 mm diameter i, inner holes 616 equally spaced with centers being 26.7 mm from the center of center hole 618
Center hole 618 has a diameter j of ⅝ inches and is threaded to accept a lower portion 546 of piston shaft 514.

Prior to use, the stainless steel screens (not shown) of the piston head 518 and cylinder 520 should be inspected for clogging, holes or over-stretching and replaced when necessary. An SFC apparatus with damaged screen can deliver erroneous SFC results, and must not be used until the screen has been replaced.

A 5.00 cm mark 556 is scribed on the cylinder 520 at a height k of 5.00 cm (±0.05 cm) above the screen (not shown) attached to the bottom 548 of the cylinder 520. This marks the fluid level to be maintained during the analysis. Maintenance of correct and constant fluid level (hydrostatic pressure) is critical for measurement accuracy.

A constant hydrostatic head reservoir 414 is used to deliver salt solution 432 to the cylinder 520 and to maintain the level of salt solution 432 at a height k of 5.00 cm above the screen (not shown) attached to the bottom 548 of the cylinder 520. The bottom 434 of the air-intake tube 410 is positioned so as to maintain the salt solution 432 level in the cylinder 520 at the required 5.00 cm height k during the measurement, i.e., bottom 434 of the air tube 410 is in approximately same plane 438 as the 5.00 cm mark 556 on the cylinder 520 as it sits on the support screen (not shown) on the ring stand 440 above the receiving vessel 424. Proper height alignment of the air-intake tube 410 and the 5.00 cm mark 556 on the cylinder 520 is critical to the analysis. A suitable reservoir 414 consists of a jar 430 containing: a horizontally oriented L-shaped delivery tube 418 for fluid delivery, a vertically oriented open-ended tube 410 for admitting air at a fixed height within the constant hydrostatic head reservoir 414, and a stoppered vent 412 for re-filling the constant hydrostatic head reservoir 414. Tube 410 has an internal diameter of xx mm. The delivery tube 418, positioned near the bottom 442 of the constant hydrostatic head reservoir 414, contains a stopcock 420 for starting/stopping the delivery of salt solution 432. The outlet 444 of the delivery tube 418 is dimensioned to be inserted through the second lid opening 536 in the cylinder lid 516, with its end positioned below the surface of the salt solution 432 in the cylinder 520 (after the 5.00 cm height of the salt solution 432 is attained in the cylinder 520). The air-intake tube 410 is held in place with an o-ring collar (not shown). The constant hydrostatic head reservoir 414 can be positioned on a laboratory jack 416 in order to adjust its height relative to that of the cylinder 520. The components of the constant hydrostatic head reservoir 414 are sized so as to rapidly fill the cylinder 520 to the required height (i.e., hydrostatic head) and maintain this height for the duration of the measurement. The constant hydrostatic head reservoir 414 must be capable of delivering salt solution 432 at a flow rate of at least 3 g/sec for at least 10 minutes.

The piston/cylinder assembly 428 is positioned on a 16 mesh rigid stainless steel support screen (not shown) (or equivalent) which is supported on a ring stand 440 or suitable alternative rigid stand. This support screen (not shown) is sufficiently permeable so as to not impede salt solution 432 flow and rigid enough to support the stainless steel mesh cloth (not shown) preventing stretching. The support screen (not shown) should be flat and level to avoid tilting the piston/cylinder assembly 428 during the test. The salt solution 432 passing through the support screen (not shown) is collected in a receiving vessel 424, positioned below (but not supporting) the support screen (not shown). The receiving vessel 424 is positioned on the balance 426 which is accurate to at least 0.01 g. The digital output of the balance 426 is connected to a computerized data acquisition system (not shown).

Preparation of Reagents (not Illustrated)

Figure 7:
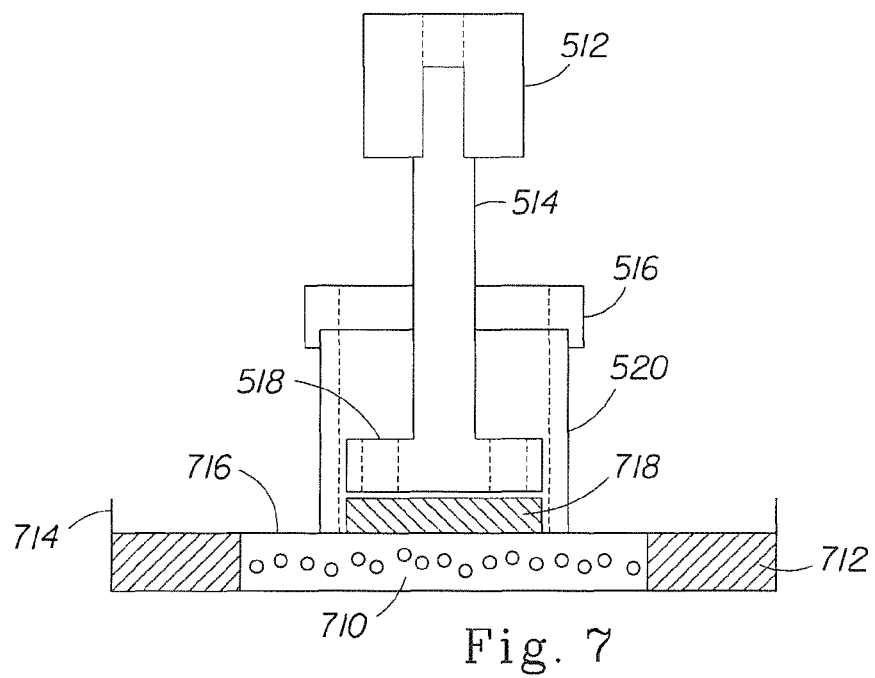
FIG. 7 is a cross-sectional side view of the piston/cylinder assembly of FIG. 5 placed on a fritted disc for the swelling phase.

Jayco Synthetic Urine (JSU) 712 (see FIG. 7) is used for a swelling phase (see SFC Procedure below) and 0.118 M Sodium Chloride (NaCl) Solution is used for a flow phase (see SFC Procedure below). The following preparations are referred to a standard 1 liter volume. For preparation of volumes other than 1 liter, all quantities are scaled accordingly.

JSU:

A 1 L volumetric flask is filled with distilled water to 80% of its volume, and a magnetic stir bar is placed in the flask. Separately, using a weighing paper or beaker the following amounts of dry ingredients are weighed to within ±0.01 g using an analytical balance and are added quantitatively to the volumetric flask in the same order as listed below. The solution is stirred on a suitable stir plate until all the solids are dissolved, the stir bar is removed, and the solution diluted to 1 L volume with distilled water. A stir bar is again inserted, and the solution stirred on a stirring plate for a few minutes more.

Quantities of salts to make 1 liter of Jayco Synthetic Urine:

Potassium Chloride (KCl) 2.00 g
Sodium Sulfate ($Na_2SO_4$) 2.00 g
Ammonium dihydrogen phosphate ($NH_4H_2PO_4$) 0.85 g
Ammonium phosphate, dibasic (($NH_4)_2HPO_4$) 0.15 g
Calcium Chloride ($CaCl_2$) 0.19 g—[or hydrated calcium chloride ($CaCl_2.2H_2O$) 0.25 g]
Magnesium chloride ($MgCl_2$) 0.23 g—[or hydrated magnesium chloride ($MgCl_2.6H_2O$) 0.50 g]

To make the preparation faster, each salt is completely dissolved before adding the next one. Jayco synthetic urine may be stored in a clean glass container for 2 weeks. The solution should not be used if it becomes cloudy. Shelf life in a clean plastic container is 10 days.

0.118 M Sodium Chloride (NaCl) Solution:

0.118 M Sodium Chloride is used as salt solution 432.

Using a weighing paper or beaker 6.90 g (±0.01 g) of sodium chloride is weighed and quantitatively transferred into a 1 L volumetric flask; and the flask is filled to volume with distilled water. A stir bar is added and the solution is mixed on a stirring plate until all the solids are dissolved.

Test Preparation

Using a solid reference cylinder weight (not shown) (40 mm diameter; 140 mm height), a caliper gauge (not shown) (e.g., Mitotoyo Digimatic Height Gage) is set to read zero. This operation is conveniently performed on a smooth and level bench top 446. The piston/cylinder assembly 428 without superabsorbent is positioned under the caliper gauge (not shown) and a reading, $L_1$, is recorded to the nearest 0.01 mm.

The constant hydrostatic head reservoir 414 is filled with salt solution 432. The bottom 434 of the air-intake tube 410 is positioned so as to maintain the top part (not shown) of the liquid meniscus (not shown) in the cylinder 520 at the 5.00 cm mark 556 during the measurement. Proper height alignment of the air-intake tube 410 at the 5.00 cm mark 556 on the cylinder 520 is critical to the analysis.

The receiving vessel 424 is placed on the balance 426 and the digital output of the balance 426 is connected to a computerized data acquisition system (not shown). The ring stand 440 with a 16 mesh rigid stainless steel support screen (not shown) is positioned above the receiving vessel 424. The 16 mesh screen (not shown) should be sufficiently rigid to support the piston/cylinder assembly 428 during the measurement. The support screen (not shown) must be flat and level.

SFC Procedure 0.9 g (±0.05 g) of superabsorbent is weighed onto a suitable weighing paper using an analytical balance. 0.9 g (±0.05 g) of superabsorbent is weighed onto a suitable weighing paper using an analytical balance. The moisture content of the superabsorbent is measured according to the Edana Moisture Content Test Method 430.1-99 ("Superabsorbent materials—Polyacrylate superabsorbent powders—MOISTURE CONTENT—WEIGHT LOSS UPON HEATING" (February 99)). If the moisture content of the polymer is greater than 5%, then the polymer weight should be corrected for moisture (i.e., the added polymer should be 0.9 g on a dry-weight basis).

The empty cylinder 520 is placed on a level benchtop 446 and the superabsorbent is quantitatively transferred into the cylinder 520. The superabsorbent particles are evenly dispersed on the screen (not shown) attached to the bottom 548 of the cylinder 520 by gently shaking, rotating, and/or tapping the cylinder 520. It is important to have an even distribution of particles on the screen (not shown) attached to the bottom 548 of the cylinder 520 to obtain the highest precision result. After the superabsorbent has been evenly distributed on the screen (not shown) attached to the bottom 548 of the cylinder 520 particles must not adhere to the inner cylinder walls 550. The piston shaft 514 is inserted through the first lid opening 534, with the lip 554 of the lid 516 facing towards the piston head 518. The piston head 518 is carefully inserted into the cylinder 520 to a depth of a few centimeters. The lid 516 is then placed onto the upper rim 544 of the cylinder 520 while taking care to keep the piston head 518 away from the superabsorbent. The lid 516 and piston shaft 526 are then carefully rotated so as to align the third, fourth, fifth, and sixth linear index marks are then aligned. The piston head 518 (via the piston shaft 514) is then gently lowered to rest on the dry superabsorbent. The weight 512 is positioned on the upper portion 528 of the piston shaft 514 so that it rests on the shoulder 524 such that the first and second linear index marks are aligned. Proper seating of the lid 516 prevents binding and assures an even distribution of the weight on the hydrogel layer 718.

Swelling Phase:

An 8 cm diameter fritted disc (7 mm thick; e.g. Chemglass Inc. # CG 201-51, coarse porosity) 710 is saturated by adding excess JSU 712 to the fritted disc 710 until the fritted disc 710 is saturated. The saturated fritted disc 710 is placed in a wide flat-bottomed Petri dish 714 and JSU 712 is added until it reaches the top surface 716 of the fritted disc 710. The JSU height must not exceed the height of the fitted disc 710.

The screen (not shown) attached to the bottom 548 of the cylinder 520 is easily stretched. To prevent stretching, a sideways pressure is applied on the piston shaft 514, just above the lid 516, with the index finger while grasping the cylinder 520 of the piston/cylinder assembly 428. This "locks" the piston shaft 514 in place against the lid 516 so that the piston/cylinder assembly 428 can be lifted without undue force being exerted on the screen (not shown).

The entire piston/cylinder assembly 428 is lifted in this fashion and placed on the fritted disc 710 in the Petri dish 714. JSU 712 from the Petri dish 714 passes through the fritted disc 710 and is absorbed by the superabsorbent polymer (not shown) to form a hydrogel layer 718. The JSU 712 available in the Petri dish 714 should be enough for all the swelling phase. If needed, more JSU 712 may be added to the Petri dish 714 during the hydration period to keep the JSU 712 level at the top surface 716 of the fritted disc 710. After a period of 60 minutes, the piston/cylinder assembly 428 is removed from the fritted disc 710, taking care to lock the piston shaft 514 against the lid 516 as described above and ensure the hydrogel layer 718 does not lose JSU 712 or take in air during this procedure. The piston/cylinder assembly 428 is placed under the caliper gauge (not shown) and a reading, $L_2$, is recorded to the nearest 0.01 mm. If the reading changes with time, only the initial value is recorded. The thickness of the hydrogel layer 718, $L_0$ is determined from $L_2-L_1$ to the nearest 0.1 mm.

The entire piston/cylinder assembly 428 is lifted in this the fashion described above and placed on the support screen (not shown) attached to the ring stand 440. Care should be taken so that the hydrogel layer 718 does not lose JSU 712 or take in air during this procedure. The JSU 712 available in the Petri dish 714 should be enough for all the swelling phase. If needed, more JSU 712 may be added to the Petri dish 714 during the hydration period to keep the JSU 712 level at the 5.00 cm mark 556. After a period of 60 minutes, the piston/cylinder assembly 428 is removed, taking care to lock the piston shaft 514 against the lid 516 as described above. The piston/cylinder assembly 428 is placed under the caliper gauge (not shown) and the caliper (not shown) is measured as $L_2$ to the nearest 0.01 mm. The thickness of the hydrogel layer 718, $L_0$ is determined from $L_2-L_1$ to the nearest 0.1 mm. If the reading changes with time, only the initial value is recorded.

The piston/cylinder assembly 428 is transferred to the support screen (not shown) attached to the ring support stand 440 taking care to lock the piston shaft 514 in place against the lid 516. The constant hydrostatic head reservoir 414 is positioned such that the delivery tube 418 is placed through the second lid opening 536. The measurement is initiated in the following sequence:

a) The stopcock 420 of the constant hydrostatic head reservoir 410 is opened to permit the salt solution 432 to reach the 5.00 cm mark 556 on the cylinder 520. This salt solution 432 level should be obtained within 10 seconds of opening the stopcock 420.

b) Once 5.00 cm of salt solution 432 is attained, the data collection program is initiated.

With the aid of a computer (not shown) attached to the balance 426, the quantity of salt solution 432 passing through the hydrogel layer 718 is recorded at intervals of 20 seconds for a time period of 10 minutes. At the end of 10 minutes, the stopcock 420 on the constant hydrostatic head reservoir 410 is closed. The piston/cylinder assembly 428 is removed immediately, placed under the caliper gauge (not shown) and a reading, $L_3$, is recorded to the nearest 0.01 mm. The final thickness of the hydrogel layer 718, $L_f$ is determined from $L_3-L_1$ to the nearest 0.1 mm, as described above. The percent change in thickness of the hydrogel layer 718 is determined from $(L_f/L_0) \times 100$. Generally the change in thickness of the hydrogel layer 718 is within about ±10%.

The data from 60 seconds to the end of the experiment are used in the SFC calculation. The data collected prior to 60 seconds are not included in the calculation. The flow rate $F_s$ (in g/s) is the slope of a linear least-squares fit to a graph of the weight of salt solution 432 collected (in grams) as a function of time (in seconds) from 60 seconds to 600 seconds.

In a separate measurement, the flow rate through the permeability measurement system 400 ($F_a$) is measured as described above, except that no hydrogel layer 718 is present. If $F_a$ is much greater than the flow rate through the permeability measurement system 400 when the hydrogel layer 718 is present, $F_s$, then no correction for the flow resistance of the permeability measurement system 400 (including the piston/cylinder assembly 428) is necessary. In this limit, $F_g=F_s$, where $F_g$ is the contribution of the hydrogel layer 718 to the flow rate of the permeability measurement system 400. However if this requirement is not satisfied, then the following correction is used to calculate the value of $F_g$ from the values of $F_s$ and $F_a$:

$$F_g=(F_a \times F_s)/(F_a-F_s)$$

The Saline Flow Conductivity (K) of the hydrogel layer 718 is calculated using the following equation:

$$K=[F_g(t=0) \times L_0]/[\rho \times A \times \Delta P],$$

where $F_g$ is the flow rate in g/sec determined from regression analysis of the flow rate results and any correction due to permeability measurement system 400 flow resistance, $L_0$ is the initial thickness of the hydrogel layer 718 in cm, $\rho$ is the density of the salt solution 432 in gm/cm$^3$. A (from the equation above) is the area of the hydrogel layer 718 in cm$^2$, $\Delta P$ is the hydrostatic pressure in dyne/cm$^2$, and the saline flow conductivity, K, is in units of cm$^3$ sec/gm. The average of three determinations should be reported.

For hydrogel layers 718 where the flow rate is substantially constant, a permeability coefficient ($\kappa$) can be calculated from the saline flow conductivity using the following equation:

$$\kappa=K\eta$$

where $\eta$ is the viscosity of the salt solution 432 in poise and the permeability coefficient, $\kappa$, is in units of cm$^2$.

In general, flow rate need not be constant. The time-dependent flow rate through the system, Fs (t) is determined, in units of g/sec, by dividing the incremental weight of salt solution 432 passing through the permeability measurement system 400 (in grams) by incremental time (in seconds). Only data collected for times between 60 seconds and 10 minutes is used for flow rate calculations. Flow rate results between 60 seconds and 10 minutes are used to calculate a value for $F_s$ (t=0), the initial flow rate through the hydrogel layer 718. $F_s$ (t=0) is calculated by extrapolating the results of a least-squares fit of $F_s$ (t) versus time to t=0.

Absorption Against Pressure

This test measures the amount of a 0.90% saline solution absorbed by superabsorbent polymers that are laterally confined in a piston/cylinder assembly under a confining pressure for a period of one hour. European Disposables and Nonwovens Association (EDANA) test method 442.2-02 entitled "Absorption Under Pressure" is used.

Basis Weight

This test measures the mass per unit area for a substrate. European Disposables and Nonwovens Association (EDANA) test method 40.3-90 entitled "Mass Per Unit Area" is used.

Liquid Strike-Through

This test measures the time it takes for a known volume of liquid applied to the surface of a substrate to pass through the substrate to an underlying absorbent pad. European Disposables and Nonwovens Association (EDANA) test method 150.4-99 entitled "Liquid Strike-Through Time" is used.

Tensile Test

This test measures the peak load exhibited by a substrate. A preferred piece of equipment to do the test is a tensile tester such as a MTS Synergie100 or a MTS Alliance, fitted with a computer interface and Testworks 4 software, available from MTS Systems Corporation 14000 Technology Drive, Eden Prairie, Minn., USA. This instrument measures the Constant Rate of Extension in which the pulling grip moves at a uniform rate and the force measuring mechanism moves a negligible distance (less than 0.13 mm) with increasing force. The load cell is selected such that the measured loads (e.g., force) of the tested samples will be between 10 and 90% of the capacity of the load cell (typically a 25N or 50N load cell).

A 1×1 inch (2.5×2.5 cm) sample is die-cut from the substrate using an anvil hydraulic press die to cut the film with the die into individual samples. A minimum of three samples are created which are substantially free of visible defects such as air bubbles, holes, inclusions, and cuts. Each sample must have smooth and substantially defect-free edges. Testing is performed in a conditioned room having a temperature of 23° C. (±1° C.) and a relative humidity of 50% (±2%) for at least 2 hours. Samples are allowed to equilibrate in the conditioned room for at least 2 hours prior to testing.

Pneumatic jaws of the tensile tester, fitted with flat 2.54 cm-square rubber-faced grips, are set to give a gauge length of 2.54 cm. The sample is loaded with sufficient tension to eliminate observable slack, but less than 0.05N. The sample is extended at a constant crosshead speed of 25.4 cm/min until the specimen completely breaks. If the sample breaks at the grip interface or slippage within the grips is detected, then the data is disregarded and the test is repeated with a new sample and the grip pressure is appropriately adjusted. Samples are run at least in triplicate to account for film variability.

The resulting tensile force-displacement data are converted to stress-strain curves. Peak load is defined as the maximum stress measured as a specimen is taken to break, and is reported in Newtons per centimeter width (as measured parallel to the grips) of the sample. The peak load for a given substrate is the average of the respective values of each sample from the substrate.

Moisture Vapor Transmission Rate (MVTR) Test

The MVTR test method measures the amount of water vapor that is transmitted through a film under specific temperature and humidity. The transmitted vapor is absorbed by CaCl2 desiccant and determined gravimetrically. Samples are evaluated in triplicate, along with a reference film sample of established permeability (e.g., Exxon Exxaire microporous material # XBF-110W) that is used as a positive control.

This test uses a flanged cup machined from Delrin (McMaster-Carr Catalog #8572K34) and anhydrous CaCl2 (Wako Pure Chemical Industries, Richmond, Va.; Catalog 030-00525).

The height of the cup is 55 mm with an inner diameter of 30 mm and an outer diameter of 45 mm. The cup is fitted with a silicone gasket and lid containing 3 holes for thumb screws to completely seal the cup.

The cup is filled with $CaCl_2$ to within 1 cm of the top. The cup is tapped on the counter 10 times, and the $CaCl_2$ surface is leveled. The amount of $CaCl_2$ is adjusted until the headspace between the film surface and the top of the $CaCl_2$ is 1.0 cm. The film is placed on top of the cup across the opening (30 mm) and is secured using the silicone gasket, retaining ring, and thumb screws. Properly installed, the specimen should not be wrinkled or stretched.

The film must completely cover the cup opening, A, which is 0.0007065 $m^2$.

The sample assembly is weighed with an analytical balance and recorded to ±0.001 g. The assembly is placed in a constant temperature (40±3° C.) and humidity (75±3% RH) chamber for 5.0 hr±5 min. The sample assembly is removed, covered with Saran Wrap® and is secured with a rubber band. The sample is equilibrated to room temperature for 30 min, the plastic wrap removed, and the assembly is reweighed and the weight is recorded to ±0.001 g. The absorbed moisture Ma is the difference in initial and final assembly weights. MVTR, in $g/m^2/24$ hr ($g/m^2/24$ hours), is calculated as:

$$MVTR = \frac{(M_a \times 24)}{(A \times 5 \text{ hours})}$$

Replicate results are averaged and rounded to the nearest 100 $g/m^2/24$ hr, e.g., 2865 $g/m^2/24$ hours is herein given as 2900 $g/m^2/24$ hours and 275 $g/m^2/24$ hours is given as 300 $g/m^2/24$ hours.

HYDROHEADX. EXAMPLES

Example 1—Polyolefin

A suitable polyolefin may be created according to the following method. An exemplary renewable resource is corn. The corn is cleaned and may be degerminated. The corn is milled to produce a fine powder (e.g., cornmeal) suitable for enzymatic treatment. The hydrolysis (e.g., liquification and saccharification) of the corn feedstock to yield fermentable sugars is well known in the agricultural and biofermentation arts. A suitable preparation pathway is disclosed in U.S. Pat. No. 4,407,955. A slurry of dry milled corn is created by adding water to the milled corn and an aqueous solution of sulfuric acid (98% acid by weight). Sufficient sulfuric acid should be added to provide a slurry pH of about 1.0 to about 2.5. The slurry is heated to about 140° C. to about 220° C. and pressurized to at least about 50 psig; however, pressures from about 100 psig to about 1,000 psig may result in greater conversion of the starch to fermentable sugars. The slurry is maintained at the aforementioned temperature and pressure for a few seconds up to about 10 minutes. The slurry may be conveyed through one or more pressure reduction vessels which reduce the pressure and temperature of hydrolyzed slurry. The slurry is subjected to standard separation techniques such as by centrifuge to yield a fermentable sugar liquor. The liquor typically has a dextrose equivalent of at least 75. The resulting sugar liquor is fermented according to processes well know to a skilled artisan using a suitable strain of yeast (e.g., genus of *Saccharomyces*). The resulting ethanol may be separated from the aqueous solution by standard isolation techniques such as evaporation or distillation.

Ethanol is dehydrated to form ethylene by heating the ethanol with an excess of concentrated sulfuric acid to a temperature of about 170° C. Ethylene may also be formed by passing ethanol vapor over heated aluminum oxide powder.

The resulting ethylene is polymerized using any of the well known polymerization techniques such as free radical polymerization, Ziegler-Natta polymerization, or metallocene catalyst polymerization. Low density branched polyethylene (LDPE) is often made by free radical vinyl polymerization. Linear low density polyethylene (LLDPE) is made by a more complicated procedure called Ziegler-Natta polymerization. The resulting polyethylene or blends thereof may be processed to yield a desired end product such as a film, fiber, or filament.

As an example, a linear low density polyethylene is made by copolymerizing ethylene with other longer chain olefins to result in a polymer having a density of about 0.915 g/cm$^3$ to about 0.925 g/cm$^3$. A 49 grams/meter (gsm) cast extruded film is made comprising the linear low density polyethylene and about 35% by weight to about 45% by weight calcium carbonate (available from English China Clay of America, Inc. under the designation Supercoat™). The film may be made porous via several routes. The film may be warmed and elongated to 500% of the film's original length using well known elongation methods and machinery. The resulting microporous film is capable of exhibiting a MVTR of at least 2000 g/m$^2$/24 hours. Alternately, the film may be incrementally stretched according to the method disclosed in U.S. Pat. No. 6,605,172. The resulting microporous film should exhibit a MVTR of at least 2000 g/m$^2$/24 hours.

A nonwoven spunbond web may be formed according to methods well known in the art such as evidenced by U.S. Pat. Nos. 4,405,297 and 4,340,563. The web is formed to have a basis weight of about 5 gsm to about 35 gsm. The individual filaments can have an average denier of about 5 or less. The individual filaments may have a variety of cross-sectional shapes. A suitable cross-sectional shape is a bilobal shape disclosed in U.S. Pat. No. 4,753,834. The resultant nonwoven may be made more hydrophilic by incorporating a surfactant in the nonwoven as described in U.S. Statutory Invention Registration No. H1670. The nonwoven treated to be more hydrophilic is suitable for use as a topsheet in an absorbent article. The nonwoven should exhibit a Liquid Strike-Through Time of less than about 4 seconds. The resultant nonwoven may be made more hydrophobic by use of a surface coating as described in U.S. Publication No. 2005/0177123A1. The nonwoven treated to be more hydrophobic is suitable for use a cuff substrate in an absorbent article. The treated nonwoven should exhibit a hydrohead of at least about 5 mbar.

Example 2—Superabsorbent Polymer

Preparation of Glycerol

Canola oil is obtained by expressing from canola seeds. Approximately 27.5 kg of canola oil, 5.3 kg methanol and 400 g sodium methoxide are charged to a 50 L round-bottomed flask equipped with a heating mantle, thermometer, nitrogen inlet, mechanical stirrer, and reflux condenser. A glass eduction tube (dip tube) is situated so that liquid can be removed from the bottom of the flask by means of a peristaltic pump. The flask is purged with nitrogen and the mixture in the flask is heated to 65° C. with stirring. The mixture is allowed to reflux for 2.5 hours, then the heat is turned off, agitation is stopped and the mixture allowed to settle for 20 minutes. The bottom layer is pumped out of the flask and kept for further use (Fraction 1). Approximately 1.4 kg methanol and 230 g sodium methoxide are added to the flask, agitation is resumed, and the mixture refluxed at 65° C. for another 2 hours. The heat is turned off, approximately 2.8 L of water are added to the flask and the mixture is stirred for 1 minute. The stirrer is turned off and the mixture allowed to settle for 20 minutes. The bottom layer is then pumped out of the flask and kept for further use (Fraction 2). Approximately 1.6 L of water is added to the flask, and the mixture is stirred for 1 minute. The stirrer is turned off and the mixture allowed to settle for 20 minutes. The bottom layer is then pumped out of the flask and kept for further use (Fraction 3). Fractions 1, 2 and 3 are combined in a suitable flask equipped with a magnetic stirrer. The combined fractions are stirred to form a homogeneous mixture and heated to 82° C. Sodium hydroxide solution (50%) is added slowly until the pH of the mixture is 11-13 and the temperature is maintained at 82° C. for a further 10 minutes. The pH is checked and more NaOH solution added if <11. The solution is concentrated at 115° C. under a vacuum of approximately 40 mm Hg until bubbling ceases (water content <5%). The solution is transferred to a round bottomed flask and the glycerol is vacuum distilled using a rotary evaporator with the oil bath temperature at 170° C. and the condenser at 130-140° C. The vacuum is controlled to achieve a moderate distillation rate. A center cut of distilled glycerol is collected.

Preparation of Acrolien

Approximately 200 g of fused aluminum oxide, 6-12 US standard mesh, primarily α-phase, is mixed with 50 g of a 20% solution of phosphoric acid for one hour. The mixture is dried under vacuum by means of a rotary evaporator with the oil bath temperature at 80° C. A stainless steel tube (chromatography column) with an internal diameter of approximately 15 mm and contour length approximately 60 cm is packed with the dried particles. The column is installed in a gas chromatogram instrument with the inlet connected to the injector port, and the outlet connected to a condenser and collection vessel. The column and injector port are heated to 300° C. and a 20% aqueous solution of glycerol derived from canola oil is injected at a rate of 40 mL/h. An inert carrier gas such as helium is optionally utilized to help transport the vapor through the column. The vapors emanating from the column outlet are condensed and collected. Acrolein is isolated from the condensate by fractional distillation or other suitable methods known to those skilled in the art.

Preparation of Acrylic Acid

A Pyrex glass reactor approximately 12 cm×2.5 cm OD equipped with a thermowell is packed with 31 g (30 mL bulk volume) of a catalyst containing 2 wt % palladium and 0.5 wt % copper supported on alumina. The reactor is heated in an oil bath at 152° C. A gaseous stream consisting of 3.4% acrolien, 14.8% oxygen, 22.9% steam, and 58.5% nitrogen by volume, is passed through the heated catalyst at such a rate that the superficial contact time was about 5 seconds. The reaction mixture is then passed through two water scrubbers connected in series held at 0° C. The aqueous solutions collected are combined and acrylic acid separated from the mixture by fractional distillation.

Preparation of Superabsorbent Polymer

L-Ascorbic Acid (0.2081 g, 1.18 mmol) is added to a 100 mL volumetric flask and is dissolved in distilled water (approximately 50 mL). After approximately ten minutes the solution is diluted to the 100 mL mark on the volumetric flask with distilled water and the flask was inverted and agitated to ensure a homogeneous solution.

To a 3 L jacketed resin kettle is added TMPTA (0.261 g, 0.881 mmol), acrylic acid (296.40 g, 4.11 mol), and distilled water (250 g). Water is circulated through the jacket of the resin kettle by means of a circulating water bath kept at 25° C. To the monomer solution is added standard 5N sodium hydroxide solution (576 mL, 2.88 mol). The resin kettle is capped with a lid having several ports. An overhead mechanical stirrer is set up using an air-tight bushing in the central port. A thermometer is inserted through a seal in another port so that the bulb of the thermometer is immersed in the mixture throughout the reaction. The solution is stirred using the overhead mechanical stirrer and purged with nitrogen using a fritted gas dispersion tube for approximately fifteen minutes. Nitrogen is vented from the kettle via an 18-gauge syringe needle inserted through a septum in the lid.

After approximately fifteen minutes the fritted gas dispersion tube is raised above the surface of the monomer solution and nitrogen was kept flowing through the headspace of the kettle. A solution of sodium persulfate (0.4906 g, 2.06 mmol) in distilled water (5 mL), and then a small aliquot of the L-ascorbic acid solution (1 mL, 1.18 mmol) is added via syringe. The mechanical stirrer is stopped when the vortex in the polymer solution disappears due to the increase in viscosity of the solution (a few seconds after adding the L-ascorbic acid solution). The polymerization reaction proceeds with the circulating bath at 25° C. for 30 minutes. After 30 minutes the temperature of the water bath is increased to 40° C. and held for an additional 30 minutes. The temperature of the water bath is then increased to 50° C. and held for another hour. The peak temperature of the static polymerization is approximately 70° C.

After one hour at 50° C. the circulating water bath is turned off. The resin kettle is opened; the polyacrylate gel is removed and broken into chunks approximately 2 cm in diameter. These are chopped into smaller particles using a food grinder attachment with 4.6 mm holes on a Kitchen-Aid mixer (Proline Model KSMS). Distilled water is added periodically from a squirt bottle to the infeed portion of the grinder to facilitate passage of the bulk gel through the grinder. Approximately 200 g of distilled water is used for this purpose. The chopped gel is spread into thin layers on two separate polyester mesh screens each measuring approximately 56 cm×48 cm and dried at 150° C. for 90 minutes in a vented oven in a fashion which allows passage of air through the mesh.

The dried gel is then milled through a Laboratory Wiley Mill using a 20-mesh screen. Care is taken to ensure that the screen does not become clogged during the grinding process. The milled dried gel is sieved to obtain a fraction with particles which pass through a No. 20 USA Standard Testing Sieve and are retained on a No. 270 USA Standard Testing Sieve. The 'on 20' and 'through 270' fractions are discarded.

The resultant free-flowing powder fraction 'through 20' and 'on 270' is dried under vacuum at room temperature until further use.

A 50% solution of ethylene carbonate (1,3-dioxolan-2-one) is prepared by dissolving 10.0 grams of ethylene carbonate in 10.0 grams of distilled water.

100.00 grams of the dried 'through 20' and 'on 270' powder above are added to a stainless steel mixing bowl (approximately 4 L) of a Kitchen Aid mixer (Proline Model KSMS) equipped with a stainless steel wire whisk. The height of the mixing bowl is adjusted until the wire whisk just contacts the bowl. The whisk is started and adjusted to a speed setting of '6' to stir the particles. Immediately thereafter, 15 grams of the above 50 wt % ethylene carbonate solution is added to the stirred AGM via a 10 mL plastic syringe equipped with a four inch 22-gauge needle. The solution is added directly onto the stirred particles over a period of several seconds. The syringe is weighed before and after the addition of solution to determine the amount added to the particles. After the solution is added, the mixture is stirred for approximately thirty seconds to help ensure an even coating. The resultant mixture is quite homogeneous with no obvious large clumps of material or residual dry powder. The mixture is then immediately transferred to a Teflon lined 20 cm×35 cm metal tray, spread into a thin layer and placed into a vented oven at 185° C. for one hour.

After one hour, the mixture is removed from the oven and allowed to cool for approximately one minute. After cooling the powder is placed in a 12 cm diameter mortar and any agglomerated pieces are gently broken apart with a pestle. The resultant powder is sieved to obtain a fraction which passes through a No. 20 US standard screen, but is retained on a No. 270 US standard screen.

The resultant 'through 20' and 'on 270' superabsorbent polymer particles are stored under vacuum at room temperature until further use. The AAP value for this material is measured according to the EDANA test method 442.2-02, and the SFC value is measured according to the SFC Test Method described above. The AAP value is found to be about 21 g/g, and the SFC value is found to be about $50 \times 10^{-7}$ $cm^3 \cdot sec/g$ The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any definition or meaning of a term in this written document conflicts with any definition or meaning of the term in a document incorporated by reference, the definition or meaning assigned to the term in this document shall govern.

What is claimed is:

1. A method for making a superabsorbent polymer for use in a disposable absorbent article, the method comprising the steps of:
   (a) providing a first volume of acrylic acid derived from a renewable resource, and made by the process comprising the steps of:
      (i) deriving an intermediate compound from a renewable resource;
      (ii) converting the intermediate compound into lactic acid and/or 3-hydroxypropionic acid;
      (iii) dehydrating the lactic acid and/or 3-hydroxypropionic acid to provide acrylic acid; and
   (b) providing a second volume of acrylic acid derived from a non-renewable resource;
   (c) combining the first volume of acrylic acid with the second volume of acrylic acid to define a final volume of acrylic acid comprising the first volume of acrylic acid with the second volume of acrylic acid; and
   (d) polymerizing the final volume acrylic acid to form a superabsorbent polymer;
   wherein the superabsorbent polymer has a $^{14}C/C$ ratio of about $1.0 \times 10^{-14}$ or greater and exhibits an Absorption Against Pressure (AAP) value of at least 15 g saline per gram of superabsorbent polymer.

2. The method of claim 1, wherein the acrylic acid is neutralized from about 50 mole % to about 95 mole %.

3. The method of claim 1, wherein the superabsorbent polymer is formed using a homogenous solution polymerization process.

4. The method of claim 1, wherein the superabsorbent polymer is formed using a multi-phase polymerization process.

5. The method of claim 4, wherein the multi-phase polymerization process is selected from the group consisting of inverse emulsion processes and suspension polymerization processes.

6. The method of claim 1, wherein the superabsorbent polymer is formed by polymerization in the presence of a di- or poly-functional monomer.

7. The method of claim 1, further comprising a step of surface-crosslinking the superabsorbent polymer.

8. The method of claim 1, wherein the superabsorbent polymer exhibits an Absorption Against Pressure (AAP) value of at least 20 g saline per gram of superabsorbent polymer.

9. The method of claim 1, wherein the superabsorbent polymer exhibits an Absorption Against Pressure (AAP) value of from about 15 g to about 25 g saline per gram of superabsorbent polymer.

10. The method of claim 1, wherein the superabsorbent polymer exhibits a saline flow conductivity (SFC) of at least $30 \times 10^{-7}$ cm$^3$·sec/g.

11. The method of claim 1, wherein the superabsorbent polymer exhibits a saline flow conductivity (SFC) of at least $50 \times 10^{-7}$ cm$^3$·sec/g.

12. A method for making a superabsorbent polymer for use in a disposable absorbent article, the method comprising the steps of:
   (a) providing a first volume of acrylic acid derived from a renewable resource;
   (b) providing a second volume of acrylic acid derived from a non-renewable resource;
   (c) combining the first volume of acrylic acid with the second volume of acrylic acid to define a final volume of acrylic acid comprising the first volume of acrylic acid with the second volume of acrylic acid; and
   (d) polymerizing the final volume acrylic acid to form a superabsorbent polymer;
   wherein the superabsorbent polymer has a $^{14}C/C$ ratio of about $1.0 \times 10^{-14}$ or greater and exhibits an Absorption Against Pressure (AAP) value of at least 15 g saline per gram of superabsorbent polymer.

13. The method of claim 12, wherein the acrylic acid is neutralized from about 50 mole % to about 95 mole %.

14. The method of claim 12, wherein the superabsorbent polymer is formed using a homogenous solution polymerization process.

15. The method of claim 12, wherein the superabsorbent polymer is formed using a multi-phase polymerization process.

16. The method of claim 15, wherein the multi-phase polymerization process is selected from the group consisting of inverse emulsion processes and suspension polymerization processes.

17. The method of claim 12, further comprising a step of surface-crosslinking the superabsorbent polymer.

18. The method of claim 12, wherein the superabsorbent polymer exhibits an Absorption Against Pressure (AAP) value of at least 20 g saline per gram of superabsorbent polymer.

19. The method of claim 12, wherein the superabsorbent polymer exhibits a saline flow conductivity (SFC) of at least $50 \times 10^{-7}$ cm$^3$·sec/g.

20. A method for making a superabsorbent polymer for use in a disposable absorbent article, the method comprising the steps of:
   (a) providing acrylic acid derived from a renewable resource;
   (b) polymerizing the acrylic acid to form an initial superabsorbent polymer;
   (c) surface-crosslinking the superabsorbent polymer to form a final superabsorbent polymer;
   wherein the final superabsorbent polymer has a $^{14}C/C$ ratio of about $1.0 \times 10^{-14}$ or greater and exhibits an Absorption Against Pressure (AAP) value of at least 15 g saline per gram of superabsorbent polymer.

* * * * *